United States Patent [19]

Hruby et al.

[11] Patent Number: 5,714,576
[45] Date of Patent: Feb. 3, 1998

[54] LINEAR ANALOGS OF ALPHA-MSH FRAGMENTS

[75] Inventors: Victor J. Hruby; Mac E. Hadley, both of Tucson, Ariz.; Fahad Al-Obeidi, Amman, Jordan

[73] Assignee: Competitive Technologies, Inc., Fairfield, Conn.

[21] Appl. No.: 826,676

[22] Filed: Apr. 7, 1997

Related U.S. Application Data

[62] Division of Ser. No. 349,902, Dec. 6, 1994, Pat. No. 5,674,839, which is a continuation of Ser. No. 916,767, Jul. 17, 1992, abandoned, which is a continuation-in-part of Ser. No. 611,456, Nov. 13, 1990, abandoned, which is a continuation of Ser. No. 212,807, Jun. 29, 1988, abandoned, which is a continuation-in-part of Ser. No. 53,229, May 22, 1987, abandoned.

[51] Int. Cl.$^6$ .............................. A61K 38/00; C07K 5/00; C07K 7/00

[52] U.S. Cl. ...................... 530/312; 530/327; 530/328; 530/329

[58] Field of Search ........................ 530/312, 327, 530/328, 329

[56] References Cited

U.S. PATENT DOCUMENTS 4,457,864  7/1984  Hruby et al. .............. 260/112.5 R

FOREIGN PATENT DOCUMENTS 0212594  8/1986  European Pat. Off. ....... A61K 37/02

*Primary Examiner*—Avis M. Davenport
*Attorney, Agent, or Firm*—Yahwak & Associates

[57] ABSTRACT

Linear and Cyclic Alpha-MSH fragment analogues of Ac-Nle$^4$-Glu$^5$-His$^6$-D-Phe$^7$-Arg$^8$-Try$^9$-Gly$^{10}$-NH$_2$. The method of stimulating melanocytes by the transdermal application of these biologically-active analogues and compositions comprising these analogues for use in the method are disclosed.

35 Claims, No Drawings

LINEAR ANALOGS OF ALPHA-MSH FRAGMENTS

The present application is a Divisional of U.S. patent application 08/349,902, filed Dec. 6th 1994 and now U.S. Pat. No. 5,674,839, which in turn is a Continuation of U.S. patent application 07/916,767, filed on Jul. 17th 1992 and now abandoned, which in turn is a Continuation-In-Part of our U.S. patent application 07/611,456, filed on Nov. 13th 1990 and now abandoned, which in turn is a Continuation of U.S. patent application 07/212,807, filed Jun. 29th 1988 and now abandoned, and which itself is a Continuation-In-Part of U.S. patent application 07/53,229 filed May 22nd 1987 and now abandoned.

In view of partial support provided by grants from the United States Public Health Service and the National Science Foundation in the making of the present invention, the United States Government has certain statutory rights to the present invention under 35 USC 200 et seq.

The present invention concerns a class of previously unreported linear and cyclic fragment analogues of alpha-MSH, the method of stimulating melanocytes in vertebrates by the transdermal application of these analogues, and compositions useful in the method.

In vertebrates, the color of their skin, fur, and feathers is determined by the number and distribution of certain color-bearing cells, e.g. melanocytes, the number of which is under genetic control. Melanocytes in mammals are localized at the basal layer of the epidermis, at the dermal-epidermal junction, and within hair follicles. Synthesis of pigment (melanin) within these melanocytes is controlled by the activity of an enzyme, tyrosinase, which is localized in an intracellular organelle, the premelanosome. Upon activation of tyrosinase, either eumelanin (brown-black) or phaeomelanin (yellow-red) pigment is deposited within the organelle; after complete melanization, the premelanosome is known as a melanosome, more specifically either an eumelanosome or a phaemelanosome depending upon color [see Fitzpatrick, T. B., Y. Hori, K. Toda, M. Seiji, Jap. J. Derm. 79:278 (1969)]. Melanosomes are delivered to surrounding keratinocytes of the skin or to cells within the shaft of the growing hair by the process known as cytocrine secretion.

Although melanin synthesis and pelage patterns are expressed genetically, follicular melanogenesis and pelage color changes in some mammals may be hormonally controlled by alpha-melanotropin (also known as alpha-melanocyte stimulating hormone, i.e. alpha-MSH), a linear tridecapeptide of the formula (SEQ. NO. 1):

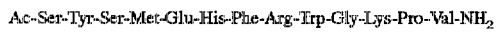

Ac-Ser-Tyr-Ser-Met-Glu-His-Phe-Arg-Trp-Gly-Lys-Pro-Val-NH$_2$

This hormone is derived from a large molecular weight precursor protein, proopiomelanocortin, and is secreted by the pars intermedia of the pituitary gland, and stimulates melanocyte adenylate cyclase activity, tyrosinase activity, and subsequent melanin production [see Hadley, M. E., C. B. Heward, V. J. Hruby, T. K. Sawyer, and Y. C. S. Young, Pigment Cell 6:323 (1980)].

In humans, alpha-MSH is apparently found only in the pituitary gland of the fetus and not in the adult. In adult humans, a certain level of melanin production is genetically determined and constitutively present. Variable melanin synthesis above and beyond this baseline level is directly dependent on UVL stimulation, e.g. sunlight; exposure to high levels of sunlight triggers increased production of melanin, with concomitant darkening of the skin. This response may be an evolutionary adaptation to protect the person against the aging and mutagenic properties of UVL. Exposure to low levels of UVL results in lower levels of integumental melanin synthesis, fading of skin color, and a diminished blocking effect allowing the skin to absorb greater amounts of radiation. Although adults do not synthesize alpha-MSH in the pituitary gland, human melanocytes will respond to this hormone (and a racemized preparation thereof).

Hypopigmentation of the skin in humans results from local defects in melanin production within the melanocytes, however, the etiology for many such hypopigmentary disturbances is still unknown.

It is estimated that approximately 1% of the world's population is afflicted with some form of hypopigmentation dysfunction. Although it is known that alpha-MSH and certain analogues of alpha-MSH can cause darkening in amphibians when administered subcutaneously, and that alpha-MSH is associated with skin darkening in adrenalectomized humans when administered intramuscularly [Lerner, A. B., and J. S. McGuire, N. E. J. Med. 270:539–546(1964)], these routes of administration are not suitable for repeated application necessary to achieve and maintain the desired effect. Prior to the present invention, no adequate means of treating these hypopigmentation disorders were known.

It has now been discovered that certain analogues of alpha-MSH can effectively be administered transcutaneously in a number of different modes, and these compounds will reach the melanocytes in active form to stimulate the production of melanin. Thus, according to the present invention, it is now possible and convenient to apply topical compositions comprising alpha-MSH analogues to achieve normalization of hypopigmentation dysfunctions such as post inflammatory hypopigmentation, including pityriasis, alba, tinea versicolor, vitiligo, idiopathic guttae hypomelanosis; and nevus depigmentosus. Furthermore, it is now possible to achieve darkening of grey hair due to aging by topical application of alpha-MSH analogues. It is also possible to enhance the value of commercial animal pelts by darkening via transdermal application of these analogues. In addition, it is now possible to achieve darkening of the skin in the total absence of sun or UV light irradiation.

All previous studies of the peptides related to alpha-MSH isolated fro the pituitary gland showed the conservation of the Met$^4$-Glu$^5$-His$^6$-Phe$^7$-Arg$^8$-Trp$^9$-Gly$^{10}$ sequence (that is Methionine-Glutamic acid-Histidine-Phenylalanine-Arginine-Tryptophan-Glycine) as the common active core. This heptapeptide sequence has been suggested to be the active site of the hormones derived from proopiomelanocortin.

Based upon the structural relationship of alpha-MSH (and its analogues and fragments) to its biological potency, using in vitro a frog skin bioassay system, the active site of alpha-MSH appears to be the common active core sequence of suitably modified Ac-Met-Glu-His-Phe-Arg-Trp-Gly-NH$_2$. This fragment (Alpha-MSH$_{4-10}$) has been synthesized and tested for its melanocyte stimulating activity in frog skin and shown to be a weak agonist when compared to the native hormone. The amino acid exchanges in position 5 (Glu) and 10 (Gly) have not, previous to the making of the present invention, been investigated. From previous research (see U.S. Pat. Nos. 4,457,864 and 4,485,039, and U.S. patent application Ser. No. 825,262) from which the present invention finds its basis, it was found that the replacement of methionine with norleucine in the active linear core heptapeptide gave a potent analogue of alpha-MSH. In addition, substitution of phenylalanine at position 7 with its enantiomer D-phenylalanine, resulted in a more biologically potent analogue having prolonged activity in both recognized (frog and lizard skin) bioassays. The following table summarizes some of these studies.

Selective Fragments of Alpha-MSH and Their Biological Activities on Frog (*Rana pipiens*) Skin and Lizard (*Anolis carolinensis*) Skin

| Peptide | Relative Potency | |
|---|---|---|
| | Frog | Lizard |
| alpha-MSH (Native hormone for comparison) | 1.0 | 1.0 |
| Ac—[Nle$^4$,D—Phe$^7$]-alpha-MSH$_{1-13}$NH$_2$ | 60.0 | 5.0 |
| Ac-alpha-MSH$_{4-10}$NH$_2$ | 0.0003 | 0.004 |
| Ac—[Nle$^4$]-alpha-MSH$_{4-10}$NH$_2$ | 0.002 | 0.06 |
| Ac—[Nle$^4$]-alpha-MSH$_{4-11}$NH$_2$ | 0.002 | 1.0 |
| Ac—[Nle$^4$, D—Phe$^7$]-alpha-MSH$_{4-10}$NH$_2$ | 0.02 | 10.0 |
| Ac[Nle$^4$, D—Phe$^7$]-alpha-MSH$_{4-11}$NH$_2$ | 0.16 | 8.0 |

The investigation of these structural-activity relationships showed two important factors: (1) the replacement of the Met amino acid with its oxidizable side chain, with the oxidatively stable amino acid, Nle, which is also an isostere for Met, resulted in about 10 times enhancement of the biological activity of the peptide fragment; and (2) replacement of L-Phe in position 7 with D-Phe and keeping Lys in position 11 further enhanced the biological activity of alpha-MSH.

In addition to the studies conducted on linear alpha-MSH analogues, a number of conformationally constrained alpha-MSH compounds have been synthesized and tested for biological potency. The first analogue studied was $$\text{Ac—[Cys}^4\text{, Cys}^{10}\text{]-alpha-MSH}_{1-13}\text{NH}_2$$

which had about 10 to 20 times the activity of the native alpha-MSH hormone in the frog skin bioassay and about two-fold the potency of alpha-MSH in the lizard skin bioassay. The design and synthesis of these prior cyclic alpha-MSH analogues were based on the consideration of the beta-turn structure at the center of the active core (His$^6$-Phe$^7$-Arg$^8$-Trp$^9$) of alpha-MSH, and the importance of this conformation pattern for biological activity.

From the classical structure activity studies of this cyclic class of alpha-MSH analogues, several conclusions were drawn: 1) cyclization between positions 4 (Met) and 10 (Gly) by isosteric replacement with cysteine amino acid enhanced the melanocyte dispersion activity by not less than 10 times in frog skin bioassay and two times in lizard skin; 2) substitution of Phe$^7$ with D-Phe$^7$ in these cyclic analogues causes double activity in frog skin and four times the activity in lizard skin bioassay; 3) the presence of Lys in position 11 always gave more active analogues than those without it; and 4) reduction or expansion of the ring size of disulfide bridge from 23-membered ring causes severe reduction in the biological potency of the resultant analogue.

The results of these studies with cyclic alpha-MSH analogues are given in the following table:

Relative In Vitro Potencies of Cyclic Alpha—MSH Analogues in the Frog and Lizard Skin Bioassays

| Peptide Analogue Amino Acids Substitution Effect | Potency | |
|---|---|---|
| | Frog | Lizard |
| Alpha—MSH (Native hormone for comparison) | 1.0 | 1.0 |
| Ac—[Cys$^4$, Cys$^{10}$]—alpha—MSH$_{1-13}$NH$_2$ | 10.0 | 2.0 |
| Ac—[Cys$^4$, Cys$^{10}$]—alpha—MSH$_{4-13}$NH$_2$ | 30.0 | 0.6 |
| Ac—[Cys$^4$, D-Phe$^7$, Cys$^{10}$]—alpha—MSH$_{4-13}$NH$_2$ | 6.0 | 6.0 |
| Ac—[Cys$^4$, Cys$^{10}$]—alpha—MSH$_{4-12}$NH$_2$ | 10.0 | 1.5 |
| Ac—[Cys$^4$, D-Phe$^7$, Cys$^{10}$]—alpha—MSH$_{4-12}$NH$_2$ | 20.0 | 6.0 |
| Ac—[Cys$^4$, Cys$^{10}$]—alpha—MSH$_{4-11}$NH$_2$ | 0.16 | 0.07 |
| Ac—[Cys$^4$, D-Phe$^7$, Cys$^{10}$]—alpha—MSH$_{4-11}$NH$_2$ | 2.5 | 3.0 |
| Ac—[Cys$^4$, Cys$^{10}$]—alpha—MSH$_{4-10}$NH$_2$ | 0.06 | 0.003 |
| Ac—[Cys$^4$, D-Phe$^7$, Cys$^{10}$]—alpha—MSH$_{4-10}$NH$_2$ | 0.75 | 0.5 |
| Ac—[Cys$^4$, Cys$^{10}$]—alpha—MSH$_{4-13}$NH$_2$ | 30.0 | 0.60 |
| [Mpa$^4$, Cys$^{10}$]—alpha—MSH$_{4-13}$NH$_2$ | 30.0 | 1.0 |
| [Maa$^4$, Cys$^{10}$]—alpha—MSH$_{4-13}$NH$_2$ | 0.06 | 0.06 |
| Ac—[Hcy$^4$, Cys$^{10}$]—alpha—MSH$_{4-13}$NH$_2$ | 0.06 | 0.70 |

In the preceeding table, the biological potencies are measured relative to alpha-MSH over the linear portion of the dose-response curve; Maa indicates 2-Mercaptoacetic acid; Mpa indicates 3-Mercaptopropionic acid; and Hcy indicates Homocysteine To further investigate the structure-potency relationship of alpha-MSH$_{4-10}$ fragments, we have systematically investigated the structural requirement for melanotropic activity of a number of previously unreported linear alpha-MSH$_{4-10}$ analogues with emphasis on the effect of substitution at positions 5 and 10.

Based on the results obtained for linear alpha-MSH analogues, we next investigated a different kind of conformationally restricted alpha-MSH analogue. Briefly, we made and concentrated on alpha-MSH$_{1-13}$, Ac-alpha-MSH$_{4-13}$ and Ac-alpha-MSH$_{4-10}$ analogues whose 4–10 structure has the general formula:

$$\text{Ac-[Nle}^4\text{, X}_{xx}^5\text{, His}^6\text{, Z}_{zz}^7\text{, Arg}^8\text{, Trp}^9\text{, Y}_{yy}^{10}\text{]-NH}_2$$

where $X_{xx}$ is either glutamic acid (Glu) or aspartic acid (Asp) (that is one of the mono amino dicarboxylic acids), $Z_{zz}$ is Phe or D-Phe and $Y_{yy}$ is a dibasic amino acid, lysine, ornithine, 2,4 diaminobutyric acid (Dab), or 2,3 diaminopropionic acid (Dpr). The alpha-MSH linear analogues listed in the following tables were synthesized by solid-phase peptide synthetic methods using p-methylbenzhydrylamine resin as a solid support, and purified by methods related to those used previously for alpha-melanotropin analogues.

group by 30 mL of 48% trifluoroacetic acid in dichloromethane containing 2% anisole, one treatment for 5 min, a second for 20 min; 3) washing with four 30 mL portions of dichloromethane, 2 min/wash; 4) neutralization by the addition of two 30 ml portions of 10% diisopropylethylamine in dichloromethane and shaking for 2 min each; 5)

Structure of Alpha-Melanotropin Analogues
Primary Sequence

| No. | 1 | 2 | 3 | 4 | 5 | 6 | 7 | 8 | 9 | 10 | 11 | 12 | 13 |
|---|---|---|---|---|---|---|---|---|---|---|---|---|---|
| alpha-MSH (native hormone) | Ac— | Ser— | Tyr— | Ser— | Met— | Glu— | His— | Phe— | Arg— | Trp— | Gly— | Lys— | Pro—Val—NH$_2$ |
| 1 | Ac— | Ser— | Tyr— | Ser— | Nle— | Glu— | His— | D—Phe— | Arg— | Trp— | Lys— | Gly— | Pro—Val—NH$_2$ |
| 2 | Ac— | Ser— | Tyr— | Ser— | Nle— | Asp— | His— | D—Phe— | Arg— | Trp— | Lys— | Gly— | Pro—Val—NH$_2$ |
| 3 | | | | Ac— | Nle— | Glu— | His— | D—Phe— | Arg— | Trp— | Lys— | Gly— | Pro—Val—NH$_2$ |
| 4 | | | | Ac— | Nle— | Asp— | His— | D—Phe— | Arg— | Trp— | Lys— | Gly— | Pro—Val—NH$_2$ |
| 5 | | | | Ac— | Nle— | Asp— | His— | D—Phe— | Arg— | Trp— | Gly— | NH$_2$ | |
| 6 | | | | Ac— | Nle— | Glu— | His— | D—Phe— | Arg— | Trp— | Lys— | NH$_2$ | |
| 7 | | | | Ac— | Nle— | Asp— | His— | D—Phe— | Arg— | Trp— | Lys— | NH$_2$ | |
| 8 | | | | Ac— | Nle— | Glu— | His— | D—Phe— | Arg— | Trp— | Orn— | NH$_2$ | |
| 9 | | | | Ac— | Nle— | Asp— | His— | D—Phe— | Arg— | Trp— | Orn— | NH$_2$ | |
| 10 | | | | Ac— | Nle— | Glu— | His— | D—Phe— | Arg— | Trp— | Dab— | NH$_2$ | |
| 11 | | | | Ac— | Nle— | Asp— | His— | D—Phe— | Arg— | Trp— | Dab— | NH$_2$ | |
| 12 | | | | Ac— | Nle— | Asp— | His— | D—Phe— | Arg— | Trp— | Dpr— | NH$_2$ | |
| 13 | | | | Ac— | Nle— | Glu— | His— | Phe— | Arg— | Trp— | Lys— | NH$_2$ | |
| 14 | | | | Ac— | Nle— | Asp— | His— | Phe— | Arg— | Trp— | Lys— | NH$_2$ | |

Structure of Alpha-Melanotropin Analogues

| No. | |
|---|---|
| (native hormone) | alpha-MSH (SEQ NO. 1) |
| 1 (SEQ NO. 2) | Ac—[Nle$^4$, D—Phe$^7$, Lys$^{10}$, Gly$^{11}$]-alpha MSH$_{1-13}$NH$_2$ |
| 2 (SEQ NO. 3) | Ac—[Nle$^4$, Asp$^5$, D—Phe$^7$, Lys$^{10}$, Gly$^{11}$]-alpha MSH$_{1-13}$NH$_2$ |
| 3 (SEQ NO. 4) | Ac—[Nle$^4$, D—Phe$^7$, Lys$^{10}$, Gly$^{11}$]-alpha MSH$_{4-13}$NH$_2$ |
| 4 (SEQ NO. 5) | Ac—[Nle$^4$, Asp$^5$, D—Phe$^7$, Lys$^{10}$, Gly$^{11}$]-alpha MSH$_{4-13}$NH$_2$ |
| 5 (SEQ NO. 6) | Ac—[Nle$^4$, Asp$^5$, D—Phe$^7$]-alpha MSH$_{4-10}$NH$_2$ |
| 6 (SEQ NO. 7) | Ac—[Nle$^4$, D—Phe$^7$, Lys$^{10}$]-alpha MSH$_{4-10}$NH$_2$ |
| 7 (SEQ NO. 8) | Ac—[Nle$^4$, Asp$^5$, D—Phe$^7$, Lys$^{10}$]-alpha MSH$_{4-10}$NH$_2$ |
| 8 (SEQ NO. 9) | Ac—[Nle$^4$, D—Phe$^7$, Orn$^{10}$]-alpha MSH$_{4-10}$NH$_2$ |
| 9 (SEQ NO. 10) | Ac—[Nle$^4$, Asp$^5$, D—Phe$^7$, Orn$^{10}$]-alpha MSH$_{4-10}$NH$_2$ |
| 10 (SEQ NO. 11) | Ac—[Nle$^4$, D—Phe$^7$, Dab$^{10}$]-alpha MSH$_{4-10}$NH$_2$ |
| 11 (SEQ NO. 12) | Ac—[Nle$^4$, Asp$^5$, D—Phe$^7$, Dab$^{10}$]-alpha MSH$_{4-10}$NH$_2$ |
| 12 (SEQ NO. 13) | Ac—[Nle$^4$, Asp$^5$, D—Phe$^7$, Dpr$^{10}$]-alpha MSH$_{4-10}$NH$_2$ |
| 13 (SEQ NO. 14) | Ac—[Nle$^4$, Lys$^{10}$]-alpha MSH$_{4-10}$NH$_2$ |
| 14 (SEQ NO. 15) | Ac—[Nle$^4$, Asp$^5$, Lys$^{10}$]-alpha MSH$_{4-10}$NH$_2$ |

The linear analogues of alpha-MSH fragments were manufactured according to the following example:

EXAMPLE I

Ac-[Nle$^4$, D-Phe$^7$, Lys$^{10}$, Gly$^{11}$]-alpha-MSH$_{1-13}$NH$_2$

This compound was prepared by coupling N$^\alpha$-Boc-Val (the term "Boc" means t-butyloxycarbonyl) to p-methylbenzhydrlamine resin (2.0 g pMBHA resin, 0.7 mmol NH$_2$/g of resin) using 3 fold excess of amino acid using solid-phase methods of peptide synthesis. After 90 min the resin washed with dichloromethane, neutralized and the amino group acetylated with acetic anhydride-pyridine mixture. No reactive amino groups on the resin were detected by ninhydrin test after 30 min. A cycle for coupling of each amino acid residue into the growing peptide chain consisted of the following: 1) washing with four 30 mL portions of CH$_2$Cl$_2$, 2 min/wash; 2) cleavage of the Boc washing with four 30 ml portions of dichloromethane, 2 min/wash; 6) addition of 2-3 equivalents of the Boc amino derivative (in this case 2.1 mmol) in 5 ml of dichloromethane, 2.4 equivalents of N-hydroxybenzotriazole of 1 mmol/ml solution of HOBt in DMF (except in the case of N-Boc-N$^{im}$Tos-His), (the term "N$^{im}$Tos" means N-imidazole tosyl), followed by 2.4 equivalents DCC of 1 mmol/ml solution of DCC in DMF. The mixture shook for 2-3 h (in case of Trp, Arg, and His, DMF was used as a coupling solvent); 7) After completion of the coupling (ninhydrin negative) washing with three 30 ml portions of dichloromethane, 2 min/wash; 8) washing with 3 ml portion of 100% ethanol, 2 min/wash; 9) Washing with four 30 ml portions of dichloromethane, 1 min/wash. The protected peptide resin corresponding to the title compound was obtained after stepwise coupling of the following N$^\alpha$-Boc amino acids (or derivatives) was performed (in order of addition): N$^\alpha$-Boc-Pro; N$^\alpha$Boc-Gly, N$^\alpha$-Boc-Lys-(N$^\epsilon$ClZ); N$^\alpha$-Boc-N$^i$-For-Trp, N$^\alpha$-Boc-N$^g$-Tos-Arg, $N^\alpha$-Boc-D-Phe, $N^\alpha$-Boc-$N^{im}$-Tos-His (the term "$N^g$" means N-guanidino; "$N^i$" means N-in dolyl, and -"2ClZ" means 2-chlorobenzyloxycarbonyl). The resulting Boc-His($N^{im}$-Tos)-D-Phe-Arg ($N^g$-Tos)-Trp($N^i$-For)-Lys($N^\epsilon$-2ClZ)-Gly-Pro-Val-p-MBHA resin was divided into four portions. One-quarter (1.0 g ~0.5 mmol) of the protected peptide-resin was converted to the protected title peptide resin after coupling $N^\alpha$-Boc-Glu-$\gamma$-Bzl, $N^\alpha$-Boc-Nle, $N^\alpha$-Boc-Ser(0-Bzl), $N^\alpha$-Boc-Tyr(0--2BrZ); $N^\alpha$-Boc-Ser(0-Bzl) (the term "2BrZ" means 2-bromobenzyloxycarbonyl). After coupling the last amino acid, the $N^\alpha$-Boc protecting group was removed, the amino acid neutralized, and the protected peptide was $N^\alpha$-acetylated with a 10-fold excess of N-acetyl-imidazole in 20 ml of dichloromethane and the resulting protected resin, Ac-Ser(0-Bzl)-Tyr(0--2BrZ)-Ser(0-Bzl)-Nle-Glu-($\gamma$-Bzl)-His($N^{im}$-Tos)-D-Phe-Arg($N^g$-Tos)-Trp($N^i$-For)-Lys($N^\epsilon$-2-ClZ)-Gly-Pro-Val-p-MBHA resin, dried in vacuo. The protected peptide resin (1.0 g) was cleaved from the resin by liquid HF. After evaporation of the volatile materials in vacuo at 0° C., the dried product was washed with ethyl ether (3×30 ml), extracted with 30% aqueous HOAc (3×30 ml), and lyophilized.

The peptide powder (530 mg) was divided into two portions (260 mg each) and one portion was dissolved in 1.5 ml of ammonium acetate buffer (pH 4.5), filtered through a cartridge filter into the top of a CMC column (2.0×30.0 cm) and eluted using 250 ml each of 0.01 (pH 4.5), 0.1M (pH 6.8), and 0.2M (pH 6.8) $NH_4OAc$. The major peak detected at 280 nm, was eluted between the end of the 0.1M and the first half of the 0.2M $NH_4OAc$ fraction and was lyophilized to give 142.3 mg of white powder. 80.0 mg of the peptide powder was purified on preparative HPLC and the major peak collected and lyophilized to give 63 mg of the title peptide.

EXAMPLE II

Ac-[Nle$^4$, Asp$^5$, D-Phe$^7$, Lys$^{10}$, Gly$^{11}$]-alpha-MSH$_{1-13}$NH$_2$ (SEQ. NO. 2)

This compound was prepared from 1.0 g (~0.5 mmol) of $N^\alpha$-Boc-His($N^{im}$-Tos)-D-Phe-Arg($N^g$-Tos)-Trp-($N^i$-For)-Lys($N^\epsilon$-2-ClZ)-Gly-Pro-Val-p-MBHA resin by stepwise coupling of $N^\alpha$-Boc-Asp(0-BZl), $N^\alpha$-Boc-Nle, $N^\alpha$-Boc-Ser(0 Bzl), $N^\alpha$-Boc-Tyr(0--2-BrZ), $N^\alpha$Boc-Ser(0-Bzl). Each coupling was achieved by the same approach mentioned previously. Acetylation of the protected tridecapapeptide-resin was carried out by 10-fold excess of N-acetylimidazole in dichloromethane (5 hr) after deprotection and neutralization of N-terminal Boc group. The Ac-Ser(0-Bzl)-Tyr(0--2-BrZ)-Ser(0-Bzl)-Nle-Asp(0-Bzl)-His($N^{im}$-Tos)-D-Phe-Arg ($N^g$-Tos)-Trp($N^i$-For)-Lys($N^\epsilon$-2-ClZ)-Gly-Pro-Val-p-MBHA resin was dried in vacuo to give 1.8 g of protected peptide resin. A 1.0 g portion of the protected peptide resin was cleaved by liquid HF and upon evaporation of the volatile materials, washed with diethylether (3×30 ml), the peptide extracted with 30% aqueous HOAc (3×30 ml), and lyophilized. A portion of the crude tridecapeptide (200 mg) was dissolved in 1.5 ml of NH$_4$OAc buffer (pH 4.5), filtered through a cartridge filter into the top of the CMC column (2.0×30.0 cm) and eluted with the same sequence of the discontinuous gradient of NH$_4$OAc as mentioned in Example I. The separated peptide after lyophilization was 152 mg. A 100 mg sample of this crude peptide was further purified by HPLC to give 67 mg of the title peptide.

EXAMPLE III

Ac-[Nle$^4$, D-Phe$^7$, Lys$^{10}$, Gly$^{11}$]-alpha-MSH$_{4-13}$NH$_2$ (SEQ. NO. 3)

From 1.0 g (0.5 mmol) of Boc-His($N^{im}$-Tos)-D-Phe-Arg ($N^g$-Tos)-TrP($N^i$-For)-Lys($N^\epsilon$-2-ClZ)-Gly-Pro-Val-p-MBHA resin the title peptide was synthesized by solid-phase technique after stepwise coupling of $N^\alpha$-Boc-Glu($\gamma$-Bzl), and $N^\alpha$-Boc-Nle. Each coupling reaction was achieved as in the previous examples except that the acetylation of the N-terminus was achieved by 2-fold excess of 1:1 acetic anhydride-pyridine in dichloromethane for 1 hr. The peptide 4 was obtained in a purified form as outlined in Example II to give a white powder with a yield of 22%.

EXAMPLE IV

Ac[Nle$^4$, Asp$^5$, D-Phe$^7$, Lys$^{10}$, Gly$^{11}$]-alpha-MSH$_{4-13}$NH$_2$ From 1.0 g (~0.5 mmol) of Boc-His($N^{im}$-Tos)-D-Phe-Arg ($N^g$-Tos)-Trp($N^i$-For)-Lys($N^\epsilon$-2-ClZ)-Gly-Pro-Val-p-MBHA resin prepared as in Example I, the title peptide was prepared by stepwise coupling of $N^\alpha$-Boc-Asp($\beta$-Bzl), and $N^\alpha$-Boc-Nle. The same technique was used as described in Example I in processing the resulting protective peptide resin. The desired peptide yielded 53 mg of HPLC pure peptide starting with 130 mg of crude peptide purified previously with CMC chromatography as outlined in Example I.

EXAMPLE V

Ac[Nle$^4$, D-Phe$^7$, Lys$^{10}$]-alpha-MSH$_{4-10}$NH$_2$

A 2.7 g resin of p-methylbenzhydrylamine (0.7 mmol NH$_2$/g resin) was suspended in dichloromethane and washed three times with 30 ml portions of dichloromethane. The washed resin was then shaken for 2 h in dichloromethane before filtering out the solvent. The swelled MBHA resin was neutralized and (coupled with the amino acids as outlined in Example I. The following amino acid derivatives were coupled into the resin (in order of their coupling): $N^\alpha$-Boc-Lys($N^\epsilon$-2-ClZ), $N^\alpha$-Boc-Trp($N^i$-For), $N^\alpha$-Boc-Arg ($N^g$-Tos), $N^\alpha$-Boc-D-Phe, $N^\alpha$-Boc-His($N^{im}$-Tos). The resulting Boc-His($N^{im}$-Tos)-D-Phe-Arg($N^g$-Tos)-Trp($N^i$-For)-Lys($N^\epsilon$-2-ClZ)-p-MBHA resin was divided into two portions. One part of the resin was coupled stepwise: $N^\alpha$-Boc-Glu($\gamma$-Bzl) and $N^\alpha$-Boc-Nle. The finished peptide resin was deboxylated and the N-terminal acetylated with 2-fold excess of a 1:1 mixture of acetic anhydride-pyridine in dichloromethane for 1 hr. The finished protected peptide resin was washed with dichloromethane and dried in vacuo to give 2.1 g. A 1.7 g portion of the protected peptide resin was cleaved by anhydrous liquid HF-anisole-dithioethane (17 ml HF, 2 ml anisole, 1 ml dithioethane). After evaporation of the volatile materials, the dried, cleaved peptide was washed with 3×30 ml of anhydrous diethylether and extracted with 3×30 ml of 30% aqueous HOAc. The aqueous extract of the peptide lyophilized to give 700 mg of crude protein. A 300 mg sample of the crude peptide was dissolved in 2 ml of NH$_4$OAc buffer (pH 4.5), and filtered through a cartridge filter on the top of a CMC column. The major peak was collected and lyphilized to give 172 mg of white powder peptide. 110 mg of the crude peptide was purified on HPLC to give 50 mg of pure title peptide.

EXAMPLE VI

Ac[Nle$^4$, Asp$^5$, D-Phe, Lye$^{10}$]-alpha-MSH$_{4-10}$NH$_2$ (SEQ. NO. 4)

The protected peptide resin to the title compound was prepared from 1.8 g of Boc-His($N^{im}$-Tos)-D-Phe-Arg($N^g$-Tos)-Trp($N^i$-For)-Lys($N^\epsilon$-2-ClZ)-p-MBHA by stepwise coupling of $N^\alpha$-Boc-Asp($\beta$-Bzl), and $N^\alpha$-Boc-Nle. Each coupling reaction was achieved with a 3-fold excess of $N^\alpha$-Boc amino acid (or derivative), a 2.4 fold excess of DCC, and a 2.4-fold excess of HOBt following the same strategy outlined previously. After coupling the last amino acid, the $N^\alpha$-Boc protection group was removed, the amino group neutralized, and acetylated with a 2-fold excess of 1:1 mixture of acetic anhydride/pyridine in dichloromethane for 1 hr. The Ac-Nle-Asp($\beta$-Bzl)-His($N^{im}$-Tos)-D-Phe-Arg($N^g$-Tos)-Trp($N^i$-For)-Lys($N^\epsilon$-2-ClZ)-p-MBHA resin was washed with dichloromethane and dried in vacuo to give 2.1 g. A 1.5 g sample of the protected peptide resin was cleaved by liquid HF and processed as in Example V to give 64 mg of the title peptide after HPLC purification of 112 mg of CMC chromatographically pure peptide.

EXAMPLE VII

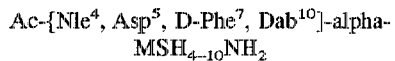

Ac-{Nle$^4$, Asp$^5$, D-Phe$^7$, Dab$^{10}$]-alpha-MSH$_{4-10}$NH$_2$

The protected peptide resin to the title compound was synthesized as in Example V except the $N^\alpha$-Boc-Dab($N_\gamma$-Z) and $N^\alpha$-Boc-Asp($\beta$-Bzl) were used instead of $N^\alpha$-Boc-Lys($N^\epsilon$-2ClZ) and $N^\alpha$-Boc-Glu($\gamma$-Bzl), respectively, in the coupling scheme to give Ac-Nle-Asp($\beta$-Bzl)-His($N^{im}$-Tos)-D-Phe-Arg($N^g$-Tos)-Trp($N^i$-For)-Dab($N^\gamma$-Z)-p-MBHA resin. Upon cleaving and processing the peptide resin as in Example V, the peptide was obtained as a white powder in 36% yield.

EXAMPLE VIII

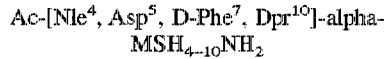

Ac-[Nle$^4$, Asp$^5$, D-Phe$^7$, Dpr$^{10}$]-alpha-MSH$_{4-10}$NH$_2$

The protected peptide resin to the title compound was synthesized as in Example V with the exception that $N^\alpha$-Boc-Dpr($N^\beta$-Z) was used instead of $N^\alpha$-Boc-Lys($N^\epsilon$-2-ClZ) and $N^\alpha$-Asp($\beta$-Bzl) for $N^\alpha$-Boc-Glu($\gamma$-Bzl) in the coupling scheme to give Ac-Nle-Asp($\beta$-Bzl)-His($N^{im}$-Tos)-D-Phe-Arg($N^g$-Tos)-Trp($N^i$-For)-Dpr($N^\beta$-Z)-p-MBHA resin. The peptide was cleaved from the resin, and processed as in Example V to give the desired peptide as a white powder: yield 36%.

EXAMPLE IX

Ac-[Nle$^4$, Lys$^{10}$]-alpha-MSH$_{4-10}$NH$_2$

The protected peptide resin to the title compound was synthesized as in Example V, with the exception that $N^\alpha$-Boc-Phe was used instead of $N^\alpha$-Boc-D-Phe in the coupling scheme to give Ac-Nle-Glu($\gamma$-Bzl)-His($N^{im}$-Tos)-Phe-Arg($N^g$-Tos)-Trp($N^i$-For)-Lys($N^\epsilon$-2-ClZ)-p-MBHA resin. The peptide was cleaved and processed to give the title compound with 40% yield.

EXAMPLE X

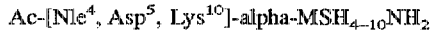

Ac-[Nle$^4$, Asp$^5$, Lys$^{10}$]-alpha-MSH$_{4-10}$NH$_2$

The protected peptide resin to the title compound was synthesized as in Example V, with the exception that $N^\alpha$-Boc-Phe was used instead of $N^\alpha$-Boc-D-Phe and $N^\alpha$-Boc-Asp($\beta$-Bzl) replaced by $N^\alpha$-Boc-Glu($\gamma$-Bzl) in the coupling scheme to give Ac-Nle-Asp($\beta$-Bzl)-Phe-Arg($N^g$-Tos)-Trp($N^i$-For)-Lys($N^\epsilon$-2-ClZ)-p-MBHA resin. The peptide was cleaved from the resin, the protecting groups removed, and the title compound purified as previously reported to give the product as a white powder in 37% yield.

The biological potencies for the linear analogues made in accordance with the preceeding examples are given in the following table in which "P" indicates prolonged action ("+"=yes, "−"=no) and "ND" indicates the sample was not run for the specific test.

| Analogue | Biological Potency | | Residual Activity | |
|---|---|---|---|---|
| | Frog | Lizard | Frog | Lizard |
| Alpha-MSH | 1.0 | 1.0 | P(−) | P(−) |
| 1 | 6.0 | 8.0 | P(+) | P(−) |
| 2 | 9.0 | 8.0 | P(+) | P(−) |
| 3 | 0.8 | 8.0 | P(+) | P(+) |
| 4 | 1.0 | 10.0 | P(+) | P(+) |
| 5 | 0.1 | 8.0 | P(−) | P(−) |
| 6 | 0.2 | 8.0 | P(−) | P(−) |
| 7 | 0.7 | 8.0 | P(−) | P(−) |
| 8 | 0.6 | 8.0 | P(−) | P(−) |
| 9 | 0.9 | 10.0 | ND | P(−) |
| 10 | 0.9 | 10.0 | P(±) | P(±) |
| 11 | 0.9 | 50.0 | P(−) | P(−) |
| 12 | 0.2 | 8.0 | P(−) | P(−) |
| 13 | 0.001 | 0.08 | P(+) | P(−) |
| 14 | 0.004 | 0.08 | P(+) | P(−) |

The results obtained with the linear conformationally restricted alpha-MSH analogues led to investigations using a different kind of restricted analogue, conformationally restricted cyclic alpha-MSH analogues.

The solid-phase peptide synthesis of cyclic melanotropin peptide analogues was conducted by conventional solid-phase synthetic techniques. In summary, $N^\alpha$-tert-butyloxycarbonyl (Boc) protected amino acids and their derivatives were coupled to a p-methylbenzhydrylamine resin with a 3-fold excess of the Boc-protected amino acid derivative, a 2.4-fold excess of N-hydroxybenzotriazole (HOBt) of 1 mmol/ml solution in DMF (except in case of His), and 2.4-fold excess of 1 mmol/ml solution dicyclohexylcarbodiimide (DCC) in DMF. The coupling reaction was carried out in dichloromethane for a 1 to 3 hour period, and was monitored by ninhydrin and/or chloranil tests and repeated as necessary. Reactive side chains of amino acids were protected as follows: Lys 2,4-dichlorobenzyloxycarbonyl; Orn, Dab, and Dpr, benzyloxycarbonyl; Trp, formyl; Arg, tosyl; His, tosyl; Glu and Asp, Benzyl ester. Cleavage of the $N^\alpha$-Boc protecting group was performed by treatment with 48% trifluoroacetic acid containing 2% anisole in dichloromethane for 5 and 20 min each.

A cycle for the incorporation of each amino acid residue into the growing peptide chain consists of the following: 1) washing with CH$_2$Cl$_2$ (4×30 ml, 1 min/wash); 2) Boc protection was removed at each step by two treatments with 48% TFA in CH$_2$Cl$_2$ containing 2% anisole for 5 and 20 min each; 3) washing with CH$_2$Cl$_2$ (2×30 ml); 4) neutralizing with 10% diisopropylethylamine in CH$_2$Cl$_2$ (2×30 ml, 3 min/wash); 5) washing with CH$_2$Cl$_2$ (3×30 ml, 2 min/wash); 6) adding the Boc-protected amino acid derivative in 20 ml CH$_2$Cl$_2$ (except in the case of Trp, Arg, or His when DMF was substituted for the CH$_2$Cl$_2$ because of the solubility problem), followed by HOBt, followed by DCC and shaking for 1–3 h; 7) washing with CH$_2$Cl$_2$ (3×30 ml, 2 min/wash); and 8) washing with 100% EtOH (3×30 ml, 2 min/wash). Completion of coupling was monitored, and after coupling the last amino acid, the $N^\alpha$-Boc protecting group was removed, the amino group neutralized, and acetylated with a 10-fold excess of N-acetylimidazole in CH$_2$Cl$_2$ or using a 1:1 mixture of acetic anhydride:pyridine in CH$_2$Cl$_2$ (2-fold excess for 1 h).

Peptides were deprotected and removed from the resin with anhydrous liquid HF (10 ml/1 g of resin) containing 10% anisole and 8% 1,2-dithioethane at 0° C. for 45 min. After evaporation of the volatile materials in vacuo, the free peptides were washed with diethylether or ethylacetate (3×30 ml) and then extracted with 30% aqueous solution of acetic acid (3×30 ml), and distilled water (3×30 ml). The combined aqueous extract was lyophilized to give a white powder of the crude peptide. Each peptide was purified by column chromatography on cation-exchange carboxymethyl cellulose (CMC) resin, using discontinuous gradient of ammonium acetate buffer as follows: 250 ml of 0.01M NH₄OAc (pH 4.5), 250 ml of 0.1M NH₄OAc (pH 6.8), and 250 ml of 0.2M NH₄OAc (pH 6.8). The major peak (280 nm detection) eluted during the last part of 0.01M NH₄OAc (pH 6.8) and the first half of the 0.1M NH₄OAc (pH 6.8) buffer was lyophilized to give a purified peptide as a white powder. The purified linear peptide was converted to the cyclic lactam analogue as outlined below.

The structures of the cyclic-melanotropin analogues which comprise a protion of the present invention are set forth in the following table.

Structure of Cyclic Alpha-Melanotropin Analogues

| No. | 1 | 2 | 3 | 4 | 5 | 6 | 7 | 8 | 9 | 10 | 11 | 12 | 13 |
|---|---|---|---|---|---|---|---|---|---|---|---|---|---|
| alpha—MSH (native hormone) | Ac | Ser | Tyr | Ser | Met | Glu | His | Phe | Arg | Trp | Gly | Lys | Pro—Val—NH₂ |
| 15 | | | | Ac | Nle | ⌈Glu | His | D-Phe | Arg | Trp | Lys⌉ | Gly | Pro—Val—NH₂ |
| 16 | | | | Ac | Nle | ⌈Glu | His | D-Phe | Arg | Trp | Lys⌉—NH₂ | | |
| 17 | | | | Ac | Nle | ⌈Asp | His | D-Phe | Arg | Trp | Lys⌉—NH₂ | | |
| 18 | | | | Ac | Nle | ⌈Asp | His | D-Phe | Arg | Trp | Orn⌉—NH₂ | | |
| 19 | | | | Ac | Nle | ⌈Asp | His | D-Phe | Arg | Trp | Dab⌉—NH₂ | | |
| 20 | | | | Ac | Nle | ⌈Asp | His | D-Phe | Arg | Trp | Dpr⌉—NH₂ | | |
| 21 | Ac | Ser | Tyr | Ser | Nle | ⌈Asp | His | D-Phe | Arg | Trp | Lys⌉ | Gly | Pro—Val—NH₂ |
| 22 | Ac | Ser | Tyr | Ser | Nle | ⌈Asp | His | D-Phe | Arg | Trp | Lys⌉—NH₂ | | |
| 23 | | Ac | Tyr | Ser | Nle | ⌈Asp | His | D-Phe | Arg | Trp | Lys⌉—NH₂ | | |
| 24 | | | Ac | Ser | Nle | ⌈Asp | His | D-Phe | Arg | Trp | Lys⌉—NH₂ | | |
| 25 | | | | Ac | Nle | ⌈Asp | His | D-Phe | Arg | Trp | Lys⌉—NH₂ | | |
| 26 | | | | Ac | Nle | ⌈Asp | His | D-Phe | Arg | Trp | Lys⌉ | Gly—NH₂ | |
| 27 | | | | Ac | Nle | ⌈Asp | His | D-Phe | Arg | Trp | Lys⌉ | Gly | Pro—NH₂ |
| 28 | | | | Ac | Nle | ⌈Asp | His | D-Phe | Arg | Trp | Lys⌉ | Gly | Pro—Val—NH₂ |
| 29 | | | Ac | Ser | Nle | ⌈Asp | His | D-Phe | Arg | Trp | Lys⌉ | Gly | Pro—Val—NH₂ |

Structure of Cyclic Alpha-Melanotropin Analogues

No.

(native hormone) alpha—MSH

15  Ac—[Nle⁴, Glu⁵, D-Phe⁷, Lys¹⁰, Gly¹¹]—alpha—MSH$_{4-13}$NH$_2$

16  Ac—[Nle⁴, Glu⁵, D-Phe⁷, Lys¹⁰]—alpha—MSH$_{4-10}$NH$_2$

17  Ac—[Nle⁴, Asp⁵, D-Phe⁷, Lys¹⁰]—alpha—MSH$_{4-10}$NH$_2$

18  Ac—[Nle⁴, Asp⁵, D-Phe⁷, Orn¹⁰]—alpha—MSH$_{4-10}$NH$_2$

19  Ac—[Nle⁴, Asp⁵, D-Phe⁷, Dab¹⁰]—alpha—MSH$_{4-10}$NH$_2$

20  Ac—[Nle⁴, Asp⁵, D-Phe⁷, Dpr¹⁰]—alpha—MSH$_{4-10}$NH$_2$

21  Ac—[Nle⁴, Asp⁵, D-Phe⁷, Lys¹⁰, Gly¹¹]—alpha—MSH

22  Ac—[Nle⁴, Asp⁵, D-Phe⁷, Lys¹⁰]—alpha—MSH$_{1-10}$NH$_2$

23  Ac—[Nle⁴, Asp⁵, D-Phe⁷, Lys¹⁰]—alpha—MSH$_{2-10}$NH$_2$

24  Ac—[Nle⁴, Asp⁵, D-Phe⁷, Lys¹⁰]—alpha—MSH$_{3-10}$NH$_2$

25  Ac—[Nle⁴, Asp⁵, D-Phe⁷, Lys¹⁰]—alpha—MSH$_{4-10}$NH$_2$

26  Ac—[Nle⁴, Asp⁵, D-Phe⁷, Lys¹⁰, Gly¹¹]—alpha—MSH$_{4-11}$NH$_2$

27  Ac—[Nle⁴, Asp⁵, D-Phe⁷, Lys¹⁰, Gly¹¹]—alpha—MSH$_{4-12}$NH$_2$

28  Ac—[Nle⁴, Asp⁵, D-Phe⁷, Lys¹⁰, Gly¹¹]—alpha—MSH$_{4-13}$NH$_2$

29  Ac—[Nle⁴, Asp⁵, D-Phe⁷, Lys¹⁰, Gly¹¹]—alpha—MSH$_{3-13}$NH$_2$

The peptide analogues according to the present invention are prepared according to the following examples:

EXAMPLE XI

Ac—[Nle⁴, Glu⁵, D-Phe⁷, Lys¹⁰, Gly¹¹]-alpha-MSH$_{4-13}$NH$_2$

Starting with 1.0 g of N$^\alpha$-Boc-Val-p-MBHA resin (0.7 mmol of N$^\alpha$-Boc-Val), the protected peptide resin for the title compound was prepared after stepwise coupling of the following N$^\alpha$-Boc-protected amino acids (in order of addition): N$^\alpha$-Boc-Pro; N$^\alpha$-Boc-Gly; N$^\alpha$-Boc-Lys(N$^\epsilon$-2,4-Cl$_2$Z); N$^\alpha$-Boc-Trp(N$^i$-For); N$^\alpha$-Boc-Arg(N$^g$-Tos); N$^\alpha$-Boc-D-Phe; N$^\alpha$-Boc-His(N$^{im}$-Tos); N$^\alpha$-Boc-Glu($\gamma$-Bzl); and N$^\alpha$-Boc-Nle. After coupling the last amino acid, the N$^\alpha$-Boc protecting group was removed, the amino group neutralized, and acetylated with either a 10-fold excess of N-acetylimidazole in dichloromethane (6–8 h) or with 2-fold excess of 1:1 mixture of acetic anhydride:pyridine in dichloromethane (1–2 hr), and the resulting protected peptide resin Ac-Nle-Glu($\gamma$-Bzl)-His(N$^{im}$-Tos)-D-Phe-Arg(N$^g$-Tos)-Trp (N$^i$-For)-Lys(N$^\epsilon$-2,4-Cl$_2$Z)-Gly-Pro-Val-p-MBHA was obtained. A 1.0 g (0.6 mmol) portion of the protected peptide resin was treated with 10 ml of anhydrous HF in the presence of 1 ml anisole and 0.8 ml 1,2-dithioethane for 45 min at 0° C. After the HF, anisole, and 1,2-dithioethane were evaporated in vacuo, the dried product mixture was washed with 3 30 ml portions of diethylether, and the peptide was extracted with three 30 ml portions of 30% acetic acid. Then, upon lyophilization of the aqueous extract of the peptide, a 325 mg of crude Ac-Nle-Glu-His-D-Phe-Arg-Trp-Lys-Gly-Pro-Val-NH$_2$ peptide, as a white powder was obtained. A 150 mg sample of crude Ac-[Nle⁴, D-Phe⁷, Lys¹⁰, Gly¹¹]-alpha-MSH$_{4-13}$NH$_2$ was subjected to the purification scheme which included dissolving the crude peptide in 2–4 ml of 0.01M NH$_4$OAc, pH 4.5, and chromatographed on carboxymethylcellulose column (2.0×25.0 cm) with a discontinuous gradient (250 ml each) of 0.01 (pH 4.5), 0.01 and 0.2M NH$_4$OAc (pH 6.8). The major peak detected at 280 nm was eluted during the first half of the 0.1M NH$_4$OAc (pH 6.8) buffer and was lyophilized to give 104 mg of a white powder. The CMC pure Ac-[Nle⁴, D-Phe⁷, Lye¹⁰, Gly¹¹]-alpha-MSH$_{4-13}$NH$_2$ was further purified by HPLC, using 0.1% trifluoroactic acid buffer and acetonitrile as organic modifier on Vydac 218TP15-16 $C_{18}$RP (25 cm×25 cm) semipreparative column. A 100 mg sample of the peptide was HPLC purified to give 74 mg pure Ac-[Nle$^4$, D-Phe$^7$, Lye$^{10}$, Gly$^{11}$]-alpha-MSH$_{4-13}$NH$_2$ peptide. A 40 mg sample of pure Ac-[Nle$^4$, D-Phe$^7$, Lys$^{10}$, Gly$^{11}$]-alpha-MSH$_{4-13}$ was dissolved in 1 ml of 5% HCL aqueous solution and chromatographed on diethylaminoethylcellulose (of hydrochloric acid form) column (1.0×15.0 cm) with 100 ml of 5% HCL aqueous solution and the eluted peak monitored at 280 nm. Lyophilization of the collected peptide peak gave 35 mg of the Ac-[Nle$^4$, D-Phe$^7$, Lys$^{10}$, Gly$^{11}$]-alpha-MSH$_{4-13}$NH$_2$×HCl salt. The peptide salt was dissolved in 3 ml of dry DMF and secondary amine free DMF (distilled from ninhydrin under reduced pressure). To the peptide solution in DMF was added anhydrous K$_2$HPO$_4$, the reaction mixture was cooled in an ice-salt bath to 0° C. and 17 μl of diphenylphosphorylazide was added and the reaction mixture stirred at 0° C. and then the whole reaction flask transferred to the cold room at 12° C. The reaction mixture was stirred overnight at 12° C. and the completion of the reaction was monitored by HPLC (Vydac column, 25.0 cm×4-6 mm with 0.1% trifluoroacetic acid/CH$_3$CN. Also, the ninhydrin test was used to detect the completion of the cyclization. The Ac-[Nle$^4$, Glu$^5$, D-Phe$^7$, Lys$^{10}$, Gly$^{11}$]-alpha-MSH$_{4-13}$NH$_2$ was purified, after quenching the reaction with 10% aqueous HOAc solution, by desalting on P$_4$ polyacryl amide column (80.0 cm×1.0 cm) using 30% HOAc and purified by semipreparative HPLC to give 16 mg of cyclic peptide

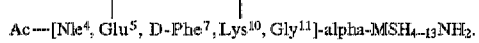
Ac—[Nle$^4$, Glu$^5$, D-Phe$^7$, Lys$^{10}$, Gly$^{11}$]-alpha-MSH$_{4-13}$NH$_2$.

EXAMPLE XII

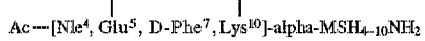
Ac—[Nle$^4$, Glu$^5$, D-Phe$^7$, Lys$^{10}$]-alpha-MSH$_{4-10}$NH$_2$

The title compound was prepared starting with 2.0 g of N$^\alpha$-Boc-Lys(N$^\epsilon$-2,4-Cl$_2$Z)-p MBHA resin (1.0 mmol/g of N$^\alpha$-Boc-Lys(N$^\epsilon$-2,4-Cl$_2$Z). The protected peptide resin to the title compound was prepared after step-wise coupling of the following N$^\alpha$-Boc-protected amino acids (in order of addition): N$^\alpha$-Boc-Trp(N$^i$-For); N$^\alpha$-Boc-Arg(N$^g$-Tos); N$^\alpha$-Boc-D-Phe; and N$^\alpha$-Boc-His(N$^{im}$-Tos). The resulting protected peptide resin, N$^\alpha$-Boc-His(N$^{im}$-Tos)-D-Phe-Arg (N$^g$-Tos)-Trp(N$^i$-For)-Lys(N$^\epsilon$-2,4-Cl$_2$Z)-p-MBHA resin was split into two halves. A 1.4 g (0.5 mmol) portion of the protected pentapeptide-resin was converted to the protected title peptide resin after coupling N$^\alpha$-Boc-Glu(γ-Bzl) and N$^\alpha$-Boc-Nle. After coupling the last amino acid, the N$^\alpha$-Boc protecting group was removed, the amino group neutralized, and acetylated as in Example XI to give the protected peptide resin Ac-Nle-Glu(γ-Bzl)-His(N$^{im}$-Tos)-D-Phe-Arg (N$^g$-Tos)-Trp(N$^i$-For)-Lys(N$^\epsilon$-2,4-Cl$_2$Z)-p-MBHA resin. A 1.0 g portion of the protected peptide resin was subjected to liquid HF cleavage and the peptide processed as in Example XI to give 356 mg of the crude Ac-[Nle$^4$, D-Phe$^7$, Lys$^{10}$]-alpha-MSH$_{4-10}$NH$_2$ peptide as a white powder. A 100.0 mg portion of the crude peptide was subjected to the purification scheme as outlined in Example XI to give 65 mg of HPLC pure Ac-[Nle$^4$, D-Phe$^7$, Lys$^{10}$]-alpha-MSH$_{4-10}$NH$_2$ peptide. 40 mg of this pure peptide was cyclized by the same approach as in Example XI to give 13 mg of HPLC pure

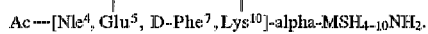
Ac—[Nle$^4$, Glu$^5$, D-Phe$^7$, Lys$^{10}$]-alpha-MSH$_{4-10}$NH$_2$.

EXAMPLE XIII

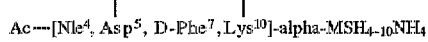
Ac—[Nle$^4$, Asp$^5$, D-Phe$^7$, Lys$^{10}$]-alpha-MSH$_{4-10}$NH$_4$

From 1.4 g (0.5 mmol) of Boc-His(N$^{im}$-Tos)-D-Phe-Arg (N$^g$-Tos)-Trp(N$^i$-For)-Lys(N$^\epsilon$-2,4-Cl$_2$Z)-p-MBHA resin the protected peptide resin of the title compound was prepared by stepwise coupling of N$^\alpha$-Boc-Asp(β-Bzl) and N$^\alpha$-Boc-Nle. Each coupling reaction was achieved by following the same coupling scheme reported under the general solid-phase peptide methodology. After coupling the last amino acid, the N$^\alpha$-Boc protecting group was removed, the amino group neutralized, and acetylayed as in Example XI, to give the protected peptide resin Ac-Nle-Asp(β-Bzl)-His(N$^{im}$-Tos)-D-Phe-Arg(N$^g$-Tos)-Trp(N$^i$-For)-Lys(N$^\epsilon$-2,4-Cl$_2$Z)-p-MBHA resin. A 1.0 g sample of the vacuum dried peptide resin was cleaved and processed as in Example XI to give 370 mg of the crude Ac-[Nle$^4$, Asp$^5$, D-Phe$^7$, Lys$^{10}$]-alpha-MSH$_{4-10}$NH$_2$. A portion of the crude heptapeptide (110 mg) was purified by the same procedure used in Example XI to give 82 mg of white powder of the linear title peptide. A 40.0 mg of the pure Ac-[Nle$^4$, Asp$^5$, D-Phe$^7$, Lys$^{10}$]-alpha-MSH$_{4-10}$NH$_2$ was subjected to cyclization to give after processing the HPLC purification, 12 mg of pure

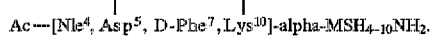
Ac—[Nle$^4$, Asp$^5$, D-Phe$^7$, Lys$^{10}$]-alpha-MSH$_{4-10}$NH$_2$.

EXAMPLE XIV

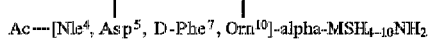
Ac—[Nle$^4$, Asp$^5$, D-Phe$^7$, Orn$^{10}$]-alpha-MSH$_{4-10}$NH$_2$ A 1.0 g of p-MBHA resin (0.7 mmol/g) was loaded with N$^\alpha$-Boc-Orn(N$_\gamma$-Z) using the coupling scheme reported in the general solid phase procedure. After 1 hr, the reaction was stopped, the resin washed, neutralized and the free amino group on the resin acetylated with 2-fold excess of 1:1 mixture of acetic anhydride:pyridine in dichloromethane for 1 h. Then the following amino acids were successfully coupled to the resin by stepwise coupling: N$^\alpha$-Boc-Trp(N$^i$-For); N$^\alpha$-Boc-Arg(N$^g$-Tos); N$^\alpha$-Boc-D-Phe; N$^\alpha$-Boc-His (N$^{im}$-Tos); N$^\alpha$-Asp(β-Bzl); and N$^\alpha$-Boc-Nle. Each coupling reaction was achieved by following the same coupling scheme outlined under the general solid phase peptide methodology. After coupling the last amino acid, the N$^\alpha$-Boc protecting group was removed, the N-terminal amino group neutralized and acetylated to give the protected peptide resin Ac-Nle-Asp(β-Bzl)-His(N$^{im}$-Tos)-D-Phe-Arg (N$^g$-Tos)-Trp(N$^i$-For)-Orn(N$_\gamma$-Z)-p-MBHA resin. A 1.0 g portion of the vacuum dried peptide resin was cleaved and processed as outlined under Example XI to give 332 mg of the crude Ac-[Nle$^4$, Asp$^5$, D-Phe$^7$, Orn$^{10}$]-alpha-MSH$_{4-10}$NH$_2$. A 105 mg portion of the crude heptapeptide was purified by the method used in Example XI to give 78 mg of white powder of the linear peptide. A 40.0 mg sample of the pure Ac-[Nle$^4$, Asp$^5$, D-Phe$^7$, Orn$^{10}$]-alpha-MSH$_{4-10}$NH$_2$ was exposed to the cyclization procedure used for Example XI, to give, after proper work-up, a product yield of 15 mg of pure

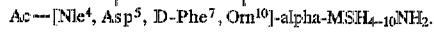
Ac—[Nle$^4$, Asp$^5$, D-Phe$^7$, Orn$^{10}$]-alpha-MSH$_{4-10}$NH$_2$.

EXAMPLE XV

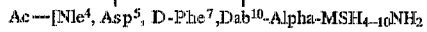
Ac—[Nle$^4$, Asp$^5$, D-Phe$^7$, Dab$^{10}$]-Alpha-MSH$_{4-10}$NH$_2$ 1.0 g of p-MBHA resin (0.7 mmol/g) was coupled with N$^\alpha$-Boc-Dab(N$_\gamma$-Z) using the coupling scheme reported in the general solid-phase procedure. After 1 hr coupling the reaction was stopped, the resin washed, neutralized and the nonreacted amino group on the resin acetylated with 1-fold excess of 1:1 mixture of acetic anhydride:pyridine in dichloromethane for 1 h. Then, the following amino acids were successively coupled to the resin by stepwise coupling: N$^\alpha$-Boc-Trp(N$^i$-For); N$^\alpha$-Boc-Arg(N$^g$-Tos); N$^\alpha$-Boc-D-Phe; N$^\alpha$-Boc-His(N$^{im}$-Tos); N$^\alpha$-Boc-Arg($\beta$-Bzl); and N$^\alpha$-Boc-Nle. After coupling the last amino acid, the N$^\alpha$-Boc protecting group was removed, the N-terminal amino group neutralized, and acetylated as in Example XI, to give the protected peptide resin Ac-Nle-Asp($\beta$-Bzl)-His(N$^{im}$-Tos)-D-Phe-Arg(N$^g$-Tos)-TrP(N$^i$-For)-Dab(N$_\gamma$-Z)-p-MBHA resin. A 1.0 g portion of the vacuum dried peptide resin was cleaved and processed to give 318.2 mg of the crude Ac-[Nle$^4$, Asp$^5$, D-Phe$^7$, Dab$^{10}$]-alpha-MSH$_{4-10}$NH$_2$. A 100.0 mg of the crude heptapeptide was purified to give 78.2 mg of white powder of the linear peptide. A 45.0 mg of the pure Ac-[Nle$^4$, Asp$^5$, D-Phe$^7$, Dab$^{10}$]-alpha-MSH$_{4-10}$NH$_2$ was cyclized and purified as previously discussed to give 13.2 mg of pure

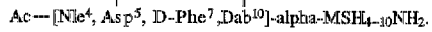
Ac—[Nle$^4$, Asp$^5$, D-Phe$^7$, Dab$^{10}$]-alpha-MSH$_{4-10}$NH$_2$.

EXAMPLE XVI

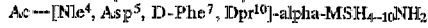
Ac—[Nle$^4$, Asp$^5$, D-Phe$^7$, Dpr$^{10}$]-alpha-MSH$_{4-10}$NH$_2$ A 1.0 g of p-MBHA resin (0.7 mmol/g) was coupled with N$^\alpha$-Boc-Dpr(N$^\beta$-Z) using the coupling scheme reported in the general solid-phase procedure. After 1 hr coupling the reaction was stopped, the resin washed, neutralized and the nonreacted amino group on the resin acetylated with 2-fold excess of 1:1 mixture of acetic anhydride:pyridine in dichloromethane for 1 h. Then the following amino acids were successively coupled to the resin by stepwise coupling: N$^\alpha$-Boc-Trp(N$^i$-For); N$^\alpha$-Boc-Arg(N$^g$-Tos); N$^\alpha$-Boc-D-Phe; N$^\alpha$-Boc-His(N$^{im}$-Tos); N$^\alpha$-Boc-Asp($\beta$-Bzl); and N$^\alpha$-Boc-Nle. After coupling, the last amino acid, the N$^\alpha$-Boc protecting group was removed, the N-terminal amino group neutralized, and acetylated as in Example XI to give the protected peptide resin Ac-Nle-Asp($\beta$-Bzl)-His(N$^{im}$-Tos)-D-Phe-Arg(N$^g$-Tos)-Trp(N$^i$-For)-Dpr($\beta$-Z)-p-MBHA resin. A 1.0 g portion of the vacuum dried peptide resin was cleaved and processed as outlined previously to give 310.8 mg of the crude Ac-[Nle$^4$, Asp$^5$, D-Phe$^7$, Dpr$^{10}$]-alpha-MSH$_{4-10}$NH$_2$. A 115.0 mg of the crude heptapeptide was purified according to the procedure of Example XI to give 82.5 mg of white powder of the linear peptide. A 38.3 mg portion of the pure Ac-[Nle$^4$, Asp$^5$, D-Phe$^7$, Dpr$^{10}$]-alpha-MSH$_{4-10}$NH$_2$ was cyclized and purified as previously discussed to give 11.3 mg of pure

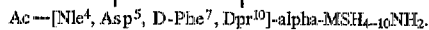
Ac—[Nle$^4$, Asp$^5$, D-Phe$^7$, Dpr$^{10}$]-alpha-MSH$_{4-10}$NH$_2$.

An additional mode of synthesis wherein the peptide is made cyclic directly on the resin has been devised.

The following protected amino acids were used for these syntheses. N$^\alpha$-Boc-Val, N$^\alpha$-Boc-Pro, N$^\alpha$-Boc-Lys(N$^\epsilon$-Fmoc), N$^\alpha$-Boc-Trp(N$^i$-For), N$^\alpha$-Boc-Arg(N$^g$-Tos), N$^\alpha$-Boc-D-Phe, N$^\alpha$-Boc-His(N$^\tau$-Bom), N$^\alpha$-Boc-Asp($\beta$-OFm), N$^\alpha$-Boc-Nle, N$^\alpha$-Boc-Ser(Bzl), N$^\alpha$-Boc-Tyr (BzlCl$_2$), and N$^\alpha$-Boc-Thr(Bzl). All amino acids were of L-configuration except for phenylalanine which was of D-configuration. All of the amino acids listed above were purchased from Bachem (Torrance, Calif.). N$^\alpha$-Boc-Orn (N$\gamma$-Fmoc) was prepared using published protocols from N$^\alpha$-Boc-Orn and fluorenylmethoxycarbonyl chloride. N$^\alpha$-Boc-Glu(N$\gamma$-OFm) was also prepared according to published procedures.

The following reagents were used for the synthesis. Trifluoroacetic acid (TFA), anhydrous anisole, 1,2-ethanedithiol acetic anhydride, pyridine, 1,3-diisopropylcarbodiimide (DIC), benzotriazol-1-yloxy-tris-(dimethylamino)-phosphonium hexafluorophosphate (BOP), piperidine, N-hydroxybenzotriazole (HOBT), and N,N-diisopropylethylamine (DIEA). All chemicals were purchased from Aldrich Chemical Co. (Milwaukee, Wis.) and were ACS grade or better grade without purification before use. The following solvents were used for synthesis: Dichloromethane (DCM), N,N-dimethylformamide (DMF), N-methylpyrrolidinone (NMP), acetonitrile, and methanol. DMF and NMP were dried over molecular sieves. The following solutions were freshly prepared before synthesis: 48% TFA/DCM/anisole (48:50:2 V/V/V), 10% DIEA/DCM (10:90 V/V), 1 mmol/mL HOBT/DMF (dissolve 15.3 gm HOBT in 100 mL DMF), 1 mmol/mL DIC/DMF (dilute 15.6 mL DIC to 100 mL with DMF), 40% piperidine/NMP (40:60 V/V).

Peptides were synthesized by utilizing a semi-automatic Vega 250 or Vega 1000 Peptide Synthesizer or by using a manual synthesizer under nitrogen bubbling. A typical coupling reaction was accomplished by using the following protocol:

| Description | Reagent/Solvent | Repeat | Time (min) |
|---|---|---|---|
| 1. Deprotect | 48% TFA | 1 | 3 |
|  |  | 1 | 20–25 |
| 2. Wash | DCM | 3 | 2 |
| 3. Neutralize | 10% DIEA/DCM | 3 | 2 |
| 4. Wash | DCM | 3 | 1 or 2 |
| 5. Monitor NH$_2$ | Ninhydrin test* | 1 | 3–5 |
| 6. Coupling BOC-AA (3X) | 1 or 2<br>HOBT(3X), DIC(3X) | | 30–60 |
| 7. Monitor NH$_2$ | Ninhydrin test* | 1 | 3–5 |
| 8. Wash | DMF | 1 | 2 |
| 9. Wash | DCM | 3 | 2 |

*Bromophenol blue test was performed on Proline residue.

Side chain cyclization to form a lactam ring was generally performed as follows: The peptide resin was treated with 40% piperidine/NMP for 45–60 min to remove Fm and Fmoc protecting groups. The resin was thoroughly washed with DMF (2 times), DCM (3 times), 10% DIEA/DCM (2 or 3 times), and DCM (3 times). Cyclization was achieved by using excess of BOP and DIEA in DMF or NMP.

The peptide resin, after cyclization, was thoroughly washed with solvent and completely dried in vacuum for one or two days before cleavage. The volume of HF, anisole and 1,2-ethandithiol differs for each peptide in the synthesis procedure. The cleavage was performed for 45–60 minutes at 0° C. and then HF was rapidly removed by vacuum at room temperature. The residue was washed with anhydrous ether three times and the peptide was extracted with 30% acetic acid (2 times), 10% acetic acid (2 times) and deionized water (2 times). The solution was lyophilized and then purified by Reverse Phase HPLC.

The crude peptide was purified by Vydac 218TP1010 C18 semipreparative column (10 mm×25 cm) on a Spectra Physics HPLC system equipped with SP8800 ternary pump, SP4270 integrator, Spectroflow 757 Absorbance Detector and monitored at 280 nm, or by Vydac 218TP152050 C18 preparative column (50 mm×25 cm) on a Rainin HPLC system equipped with HPLX solvent delivery system with 2 pumps, Rainin pressure module, Rainin Kipp & Zonen Integrator, Dynamax Absorbance Detector Module UV-D and monitored at 254 nm and 284 nm. The purity of the purified peptide was checked by TLC in three different solvents and by analytical HPLC (Vydac 218TP104 C18) at 280 nm and 230 nm and every peptide was greater than 95% pure. The structures of the pure peptides were confirmed by fast atom bombardment (FAB) mass spectrometry.

EXAMPLE XVII

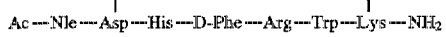

This peptide has been synthesized in small scale by both solution phase synthesis and solid phase synthesis. This example is directed to a modified larger scale synthesis. To a suspension of pMBHA resin (10 g, 3.6 mmol) in DCM (100 mL) was added $N^\alpha$-Boc-Lys($N^\epsilon$-Fmoc) (4.21 g, 9 mmol) and HOBT/DMF (9 mL, 9 mmol). After the mixture was shaken for 10 min, DIC/DMF (9 mL, 9 mmol) was aded. The mixture was shaken for 35 min and, at this time, the resin gave a negative ninhydrin test. Stepwise coupling of $N^\alpha$-Boc-Trp($N^i$-For), $N^\alpha$-Boc-Arg($N^g$-Tos), $N^\alpha$-Boc-D-Phe, $N^\alpha$-Boc-His($N^\pi$-Bom) and $N^\alpha$-Boc-Asp($\beta$-OFm) was accomplished using the previous protocol. After coupling the last amino acid, the Fm and Fmoc protecting groups were removed by treating the peptide resin with 40% piperidine/NMP (100 mL) for 45 min. The side chain cyclization between Asp and Lys was acheived by using BOP (12.7 g, 8-fold), DIEA (4.7 g, 10-fold) in 100 mL DMF for 6 h and the resin gave a negative ninhydrin test. The Boc group was removed, $N^\alpha$-Boc-Nle was coupled to the resin and acetylated with 4 mL acetic anhydride, 4 mL pyridine in 100 mL DCM for 60 min. After thoroughly washing, the resultant resin was dried in vacuum overnight to give 13.6 g of the protected peptide resin. A portion of the resin (7.2 g) was cleaved by anhydrous HF (110 mL) in the presence of anisole (7 mL) and 1,2-ethanedithiol (7 mL) for 45 min at 0° C. After evaporation of the HF, anisole, ethanedithiol by vacuum, the residue was washed 3 times with anhydrous ether and the peptide was extracted with 30% acetic acid several times (total 200 mL) and then with 10% acetic acid several times (total 200 mL). The combined aqueous extracts were lyophilized for 2 days to give 1.85 g of crude peptide. This crude peptide was purified by a Vydac 2 inch C18 column on a Rainin HPLC system. About 200–220 mg of crude product was used per injection and four fractions have been collected after every run. From all 1.85 g of crude product there was obtained the following: (67 mg 95% pure; 536 mg 99% pure; 76 mg 86% pure; 35 mg 45% pure).

EXAMPLE XVIII

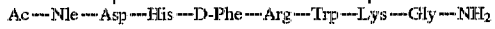

The protected peptide resin to the title compound was prepared from 2.27 g of pMBHA resin (1.11 mmol, 0.49 mmol NH$_2$/g resin) by stepwiswe coupling of $N^\alpha$-Boc-Gly, $N^\alpha$-Boc-Lys($N^\epsilon$-Fmoc), $N^\alpha$-Boc-Trp($N^i$-For), $N^\alpha$-Boc-Arg($N^g$-Tos), $N^\alpha$-Boc-D-Phe, $N^\alpha$-Boc-His($N^\pi$-Bom) and $N^\alpha$-Boc-Asp($\beta$-OFm) using the previous protocol. After coupling the last amino acid, the Fm and Fmoc protecting groups were removed by treating the peptide resin with 40% piperidine/NMP (40 mL) for 60 min. The cyclization was acheived by using BOP (3.94 g, 8-fold), DIEA (2.0 mL, 8-fold) in 40 mL DMF for 14 hr and at this time the resin gave a negative ninhydrin test. The Boc group was removed, $N^\alpha$-Boc-Nle was coupled and acetylated with 1 mL acetic anhydride, and 1 mL pyridine in 25 mL DCM for 60 min to give 3.32 g of resin. A portion of this resin (2.32 g) was cleaved by anhydrous HF (25 mL) in the presence of anisole (2 mL) and 1,2-ethanedithiol (1 mL) for 1 hr at 0° C. After workup and lyophilization, a crude peptide (840 mg) was obtained. A portion (210 mg) of this peptide was purified by HPLC to give peptide (72 mg, larger than 95% pure).

EXAMPLE XIX

The protected peptide resin to the title compound was prepared from the peptide resin, H-Asp-His($N^\pi$-Bom)-D-Phe-Arg($N^g$-Tos)-Trp($N^i$-For)-Lys-Gly-Pro-pMBHA which was synthesized according to the previous protocol. A portion of resin (1.06 g, 0.32 mmol) was added to $N^\alpha$-Boc-Nle and acetylated with 0.5 mL acetic anhydride, and 0.5 mL pyridine in 10 mL DCM for 30 min to give 1.1 g of resin. This resin was cleaved by anhydrous HF (12 mL) in the presence of anisole (0.8 mL) and 1,2-ethanedithiol (0.8 mL) for 1 hr at 0° C. After workup and lyophilization a crude peptide (250 mg) was obtained. This was purified by HPLC to give peptide (43 mg, greater than 95% pure) plus some less pure fractions.

EXAMPLE XX

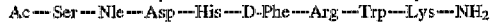

The protected peptide resin to the title compound was prepared from 5 g of pMBHA resin (2.0 mmol, 0.4 mmol NH$_2$/g resin) by stepwise coupling of $N^\alpha$-Boc-Lys($N^\epsilon$-Fmoc), $N^\alpha$-Boc-Trp($N^i$-For), $N^\alpha$-Boc-Arg($N^g$-Tos), $N^\alpha$-Boc-D-Phe, $N^\alpha$-Boc-His($N^\pi$-Bom) and $N^\alpha$-Boc-Asp($\beta$-OFm) using the general protocol. After coupling the last amino acid, the Fm and Fmoc protecting groups were removed by treating the peptide resin with 40 mL of 40% piperidine/NMP for 45 min. Cyclization was achieved by using BOP (5.3 g, 6-fold) and DIEA (2.8 mL, 8-fold) in NMP (40 mL) for 6 hr. Cyclization was repeated again, however, the ninhydrin test remained light blue-purple. The free amino group was capped by using acetic anhydride (1.2 mL), pyridine (1.2 mL) in DCM (60 mL) for 35 min. After the Boc group was removed, $N^\alpha$-Boc-Nle was added to the resin, and the Boc group was removed to give 8.2 g of H-Nle-Asp-His($N^\pi$-Bom)-D-Phe-Arg($N^g$-Tos)-Trp($N^i$-For)-Lys-pMBHA peptide resin. A portion of the resin (1.64 g, 0.4 mmol) was added to $N^\alpha$-Boc-Ser(Bzl) and acetylated with 1 mL acetic anhydride, 1 mL pyridine for 1.5 hr to give 1.78 g of resin to the title compound. This resin was cleaved by anhydrous HF (20 mL) in the presence of anisole (1 mL) and 1,2-ethanedithiol (1.2 mL) for 1 hr at 0° C. After workup and lyophilization to give crude peptide. It was purified by HPLC on a 2 inch column to give peptide (232 mg, 96% pure).

EXAMPLE XXI

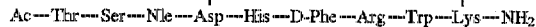

Ac—Thr—Ser—Nle—Asp—His—D-Phe—Arg—Trp—Lys—NH$_2$

The resin (3.28 g, 0.8 mmol), H-Nle-Asp-His($N^\pi$-Bom)-D-Phe-Arg($N^g$-Tos)-Trp($N^i$-For)-Lys-pMBHA, was synthesized as described above. After the addition of $N^\alpha$-Boc-Ser (Bzl) and $N^\alpha$-Boc-Thr(Bzl) and subsequent removal of the Boc group, the thoroughly washed resin was split in to two equal parts (one part was acetylated by acetic acid and pyridine to give the peptide resin according to the title compound). The second peptide resin was cleaved by anhydrous HF in the presence of anisole and 1,2-ethanedithiol for 1 h at 0° C. After workup and lyophilization to a crude peptide (450 mg) which was purified by HPLC to give peptide (210 mg, about 90% pure).

EXAMPLE XXII

Ac—Ser—Thr—Ser—Nle—Asp—His—D-Phe—Arg—Trp—Lys—NH$_2$

The second part of resin from the above procedure, after addition of $N^\alpha$-Boc-Ser(Bzl) and acetylation with acetic anhydride/pyridine gave the protected peptide resin to the title compound. The peptide resin was cleaved by anhydrous HF in the presence of anisole and 1,2-ethanedithiol for 1 h at 0° C. After workup and lyophilization to give crude peptide (465 mg). It was purified by HPLC to give peptide (231 mg, about 95% pure).

EXAMPLE XXIII

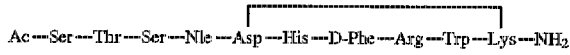

Ac—Nle—Asp—His—D-Phe—Arg—Trp—Lys—Gly—Pro—Val—NH$_2$

The protected peptide resin to the title compound was prepared from 3.4 g of pMBHA resin (1.19 mmol, 0.35 mmol NH$_2$/g resin) by stepwise coupling of $N^\alpha$-Boc-Val, $N^\alpha$-Boc-Pro, $N^\alpha$-Boc-Gly, $N^\alpha$-Boc-Lys($N^\epsilon$-Fmoc), $N^\alpha$-Boc-Trp($N^i$-For), $N^\alpha$-Boc-Arg($N^g$-Tos), $N^\alpha$-Boc-D-Phe, $N^\alpha$-Boc-His($N^\pi$-Bom) and $N^\alpha$-Boc-Asp($\beta$-OFm) according to the previous protocol. After coupling the last amino acid, the Fm and Fmoc protecting groups were removed by treating the peptide resin with 40% piperidine/NMP for 45 min. Cyclization was achieved by using BOP (2.1 g, 4-fold) and DIEA (1.3 mL, 6-fold) in 60 mL solvent (DMF:NMP 1:1) overnight. The coupling was repeated once at which time the resin gave a negative ninhydrin test. The Boc group was removed and $N^\alpha$-Boc-Nle was added to the resin according to the general protocol to give 5.5 g of peptide resin. A portion of the resin (1.65 g, 0.35 mmol), after removal of the Boc group and acetylation with 0.5 ml acetic anhydride and 0.5 mL pyridine, yielded 1.67 g of resin according to the title compound. This resin was cleaved by anhydrous HF (20 mL) in the presence of anisole (1.3 mL) and 1,2-ethanedithiol (1.3 mL) for 1 hr at 0° C. After workup and lyophilization to give the crude peptide which was purified by HPLC to give peptide (262 mg, 93% pure). A portion of this peptide was further purified on a semipreparative column.

EXAMPLE XXIV

Ac—Ser—Nle—Asp—His—D-Phe—Arg—Trp—Lys—Gly—Pro—Val—NH$_2$

The protected peptide resin to the title compound was prepared from 3 g pMBHA resin (1.05 mmol, 0.35 mmol NH$_2$/g resin) by stepwise coupling of $N^\alpha$-Boc-Val, $N^\alpha$-Boc-Pro, $N^\alpha$-Boc-Gly, $N^\alpha$-Boc-Lys($N^\epsilon$-Fmoc), $N^\alpha$-Boc-Trp($N^i$-For), $N^\alpha$-Boc-Arg($N^g$-Tos), $N^\alpha$-Boc-D-Phe, $N^\alpha$-Boc-His ($N^\pi$-Bom) and $N^\alpha$-Boc-Asp($\beta$-OFm) according to the general protocol. After coupling the last amino acid, the Fm and Fmoc protecting groups were removed by treating the peptide resin with 40% piperidine/NMP for 35 min. Cyclization was acheived by using BOP (1.86 g, 4-fold), DIEA (1.1 mL, 6-fold) in 40 mL solvent (DMF:NMP 1:1) overnight, and the resulting ninhydrin test was light purple. The free amino group was capped by using acetic anhydride (1.2 mL), pyridine (1.2 mL) in DCM (30 mL) for 15 mL. After the Boc group was removed and $N^\alpha$-Boc-Nle, $N^\alpha$-Boc-Ser (Bzl) was added to the resin according to the general protocol 5.5 g of peptide resin was obtained. Half of the resin (2.75 g, 0.52 mmol) was acetylated with 1 mL acetic anhydride, 1 mL pyridine to give 2.26 g of resin to the title compound. This resin was cleaved by anhydrous HF (23 mL) in the presence of anisole (1.5 mL) and 1,2-ethanedithiol (1.5 mL) for 1 hr at 0° C. After workup and lyophilizaton, it was purified by HPLC on 2 inch column to give the titled peptide (535 mg, 94% pure). A portion (100 mg) of this peptide was further purified on a semipreparative column.

EXAMPLE XXV

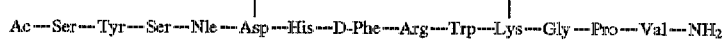

Ac—Ser—Tyr—Ser—Nle—Asp—His—D-Phe—Arg—Trp—Lys—Gly—Pro—Val—NH$_2$

The resin (2.75 g, 0.52 mm0l), Boc-Ser(Bzl)-Nle-Asp-His($N^\pi$-Bom)-D-Phe-Arg($N^g$-Tos)-Trp($N^i$-For)-Lys-Gly- Pro-Val-pMBHA, was synthesized from previous reaction. After the Boc group was removed, $N^\alpha$-Boc-Tyr(BzlCl$_2$) and $N^\alpha$-Boc-Ser(Bzl) were added to the resin and it was acetylated with 1 mL acetic anhydride and 1 mL pyridine to give 3.0 g of resin to the titled compound. Half of this resin (1.5 g) was cleaved by anhydrous HF (15 mL) in the presence of anisole (1.0 mL) and 1,2-ethanedithiol (1.0 mL) for 1 hr at 0° C. After workup and lyophilization to the crude peptide, it was purified by HPLC on a 2 inch column to give peptide (210 mg, 90% pure). A portion of this peptide was further purified on a semipreparative column.

The biological potencies of alpha-MSH, the linear and cyclic analogues were determined by their ability to stimulate melanosome dispersion in vitro in the frog and lizard bioassays. This in vitro assay provides clear cut dose response curves (between $2.5 \times 10^{-11}$ and $4 \times 10^{-10}$ M) and can detect minimal concentration of alpha-MSH of about $10^{-11}$ M. The assay is based upon the centrifugal dispersion of melanosomes (melanin granules) within the dendritic processes of integumental dermal melanophores leading to darkening of the skin. All the test solutions were prepared via serial dilutions from a stock solution ($10^{-4}$ M). The frogs (*Rana pipiens*) used in these evaluations were obtained from Kons Scientific, Germantown, Wis., and the lizards (*Anolis carolinensis*) were from the Snake Farm, La Place, La. Biological activities of the cyclic alpha-melanotropin analogues are reported in the following table:

| Analogue | Biological Potency | | Residual Activity | |
|---|---|---|---|---|
| | Frog | Lizard | Frog | Lizard |
| alpha-MSH | 1.0 | 1.0 | p(−) | p(−) |
| 15 | 1.0 | 6.0 | p(+) | p(+) |
| 16 | 0.5 | 9.0 | p(+) | p(+) |
| 17 | 0.5 | 90.0 | p(+) | p(+) |
| 18 | 1.0 | 20.0 | p(−) | p(−) |
| 19 | 1.0 | 5.0 | p(−) | p(−) |
| 20 | 0.01 | 5.0 | p(−) | p(−) |
| 21 | 8.0 | | p(+) | |
| 22 | 2.0 | | p(+) | |
| 23 | 0.7 | | p(+) | |
| 24 | 1.0 | | p(+) | |
| 25 | 5.0 | | p(+) | |
| 26 | 5.5 | | p(+) | |
| 27 | 4.0 | | p(+) | |
| 28 | 2.0 | | p(+) | |
| 29 | 9.0 | | p(+) | |

Our previous patents (U.S. Pat. Nos. 4,457,864 and 4,485,039), the disclosures of which are incorporated herein in toto by reference, indicated the importance of conformational restriction of the active site of alpha-MSH. Cyclization constraint of alpha-MSH at positions 4 and 10 using peudoisosteric replacement of Met-4 and Gly-10 with Cys amino acids resulted in many fold enhancement in melanocyte dispersions activity of the synthesized analogue. The potency enhancement of the cyclic analogues compared to that of their linear ancestor was clearly dependent on the bioassay system used. Our major interest was to get analogues with high potency on lizard skin since the activity of the latter bioassay is linearly correlated to the activity in the mammalian systems. The major characteristic of

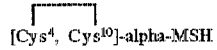
[Cys$^4$, Cys$^{10}$]-alpha-MSH cyclic analogues was that it showed low activity in lizard skin bioassay and high potency in frog skin; also with 500-fold reduction in activity upon ring size reduction (22-membered ring) or increase (24-membered ring) in comparison with the optimized ring size (23-membered ring). The conformational constraint of alpha-MSH by lactam linkage between amino acids in positions 5 and 10 resulted in a group of cyclic compounds which comprise a portion of the present invention. The ring size centered at 23-membered ring, compound 17 gave the highest biological potency in lizard skin with not much change in potency in frog skin assay. The enhancement in potency between the cyclic and its linear ancestor is in the order of ten times of magnitude. The potency of cyclic analogue 16 is not much affected in comparison to the linear but with one important change with the appearance of prolonged activity in the cyclic analogue. The C-terminal tripeptide, Gly-Pro-Val has no effect on the potency of these analogues as is revealed in compound 15. There is one important factor in these cyclic lactam peptides, which is the prolongation in activity of the cyclic in comparison to that found in the linear. The compounds of the present invention are superior to alpha-MSH in one or more of the following characteristics: potency as measured by the in vivo and in vitro frog and/or lizard assay; duration of in vivo effect in such assays; and/or resistance to degradation by blood serum enzymes.

The compounds useful in this invention may be administered transdermally, and by the term "transdermal" is meant any method by which the compounds according to the present invention are introduced across an epidermal layer of cells. For example, transdermal as used in this disclosure encompasses the administration of the compound by topical methods; by intravenous, intramuscular or subcutaneous injection; by solution for use as ocular drops, nasal sprays or tracheal sprays; by the oral route of administration such as by pills, troches, etc.; and by suppositories for vaginal or anal routes of administration. The compound will be formulated in suitable compositions determined by the intended means of administration, according to methods and procedures well-known to those skilled in the art. For example, the compounds suitable for use in this invention may be formulated or compounded into pharmaceutical compositions comprising at least one compound of the present invention (the compositions according to the present invention may comprise one compound or admixtures of compounds according to the present present) in admixture with a solid or liquid pharmaceutical excipeint such as a diluent or carrier for enteral or parenteral administration. As injection medium, water containing the usual pharmaceutical additives for injection solutions, such as stabilizing agents, solubiliizing agents, and buffers is preferred. Among additives of this type are, for example, tartrate and citrate buffers, ehtanol, complex forming agents such as ethylenediaminetetraacetic acid, and high molecular weight polumers such as liquid polyethylene oxide for viscosity regulation. Solid carrier materials include, for example, starch, lactose, mannitol, methyl cellulose, talc, highly dispersed silicic acid, high molecular weight fatty acids such as stearic acid, gelatine, agar-agar, calcium phosphate, magnesium stearate, animal and vegetable fats, and high molecular weight polymers such as polyethylene glycols. Compositions suitable for oral administration can, if desired, contain flavoring and/or sweetening agents. For topical administration, the compounds may be preferrably used with various conventional bases for topical preparations such as creams, ointments, gels, lotions, or sprays, depending upon the desired mode of delivery of the ingredients to an individual. In manufacturing these preparations, the composition may also be mixed with conventional inert excipients such as thickening agents, emollients, surfactants, pigments, perfumes, preservatives, fillers, and emulsifiers, all of which are well known and conventionally used in the formulation of transdermal or other preparations. Typically, these non-active ingredients will make up the greater part of the final preparation. Preferably, the compositions are manufactured to allow for slow-release or timed-release delivery.

The actual amount of administered compound according to the present invention may vary between fairly wide ranges depending upon the mode of administration, the excipients used, and the degree of stimulation desired. Such amounts are well within the skill of the pharmaceutical scientist to determine, and the amount administered to the mammal being administered to may be any amount chosen to stimulate melanotropic activity.

The remarkable properties of compounds of the invention also render them useful as substitutes for alpha-MSH and [Nle$^4$]-alpha-MSH in existing diagnostic, therapeutic and basic research schemes. In the area of diagnostic procedures, it is apparent that compounds of the invention, especially those which have been radioiodinated or coupled with gamma radiation emitters, are exceptionally well suited for use in locating and/or differentially characterizing melanoma cells on the basis of association with melanotropin receptors in such cells. The serum stability of compounds of the invention makes them prime candidates in proposed selective drug delivery systems wherein target tissues are known to have high concentrations of melanotropin receptors, and wherein the compounds according to the present invention may be used as a ligand to deliver an anti-cancer or diagnostic molecule (a radioactive label, for example, which can be used to locate melanotropin receptors in the body). The relative high potency and prolonged activity of compounds of the invention in color change-associated phenomena is expected to be duplicated in the context of other biological effects previously noted for naturally occurring melanocyte stimulating hormone and its synthetic analogues.

A listing of all amino acid sequences described in the preceding specification is as follows:

Thus while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Such variations and modifications, for example, would include the substitution of structurally similar amino acid sequences provided herein which function to yield substantially similar melanocyte stimulation to those specifically described above. Thus, changes in sequence by the substitution, deletion, insertion or addition of amino acids (in the peptide sequences) which do not substantially alter the function of those sequences specifically described above are deemed to be within the scope of the present invention. Accordingly, such changes and alterations are properly intended to be within the full range of equivalents, and therefore within the purview of the following claims.

Having thus described our invention and the manner and a process of making and using it in such full, clear, concise and exact terms so as to enable any person skilled in the art to which it pertains, or with which it is most nearly connected, to make and use the same.

We claim:

1. A linear analogue of alpha-MSH which is selected from the group consisting of (a) an alpha-MSH$_{1-13}$NH$_2$ analogue, (b) an Ac-alpha MSH$_{4-13}$NH$_2$ analogue, and (c) an Ac-alpha-MSH$_{4-10}$ analogue wherein the 4–10 structure of said analogue has the general formula:

Ac-[Nle$^4$, Xxx$^5$, His$^6$, Zzz$^7$, Arg$^8$, Trp$^9$, Yyy$^{10}$]-NH$_2$ wherein Xxx is Asp or Glu; wherein Zzz is D-Phe or Phe; and wherein Yyy is Lys, Gly, Orn, Dab or Dpr.

2. A linear alpha-MSH analogue according to claim 1 which is selected from the group consisting of

```
Ac—Ser—Tyr—Ser—Nle—Glu—His—D—Phe—Arg—Trp—Lys—Gly—Pro—Val—NH2
Ac—Ser—Tyr—Ser—Nle—Asp—His—D—Phe—Arg—Trp—Lys—Gly—Pro—Val—NH2
         Ac—Nle—Glu—His—D—Phe—Arg—Trp—Lys—Gly—Pro—Val—NH2
         Ac—Nle—Asp—His—D—Phe—Arg—Trp—Lys—Gly—Pro—Val—NH2
         Ac—Nle—Asp—His—D—Phe—Arg—Trp—Gly—NH2
         Ac—Nle—Glu—His—D—Phe—Arg—Trp—Lys—NH2
         Ac—Nle—Asp—His—D—Phe—Arg—Trp—Lys—NH2
         Ac—Nle—Glu—His—D—Phe—Arg—Trp—Orn—NH2
         Ac—Nle—Asp—His—D—Phe—Arg—Trp—Orn—NH2
         Ac—Nle—Glu—His—D—Phe—Arg—Trp—Dab—NH2
         Ac—Nle—Asp—His—D—Phe—Arg—Trp—Dab—NH2
         Ac—Nle—Asp—His—D—Phe—Arg—Trp—Dpr—NH2
         Ac—Nle—Glu—His—Phe—Arg—Trp—Lys—NH2
         Ac—Nle—Asp—His—Phe—Arg—Trp—Lys—NH2.
```

3. A linear alpha-MSH analogue according to claim 2 which is: Ac-Ser-Tyr-Ser-Nle-Glu-His-D-Phe-Arg-Trp-Lys-Gly-Pro-Val-NH$_2$.

4. A linear alpha-MSH analogue according to claim 2 which is: Ac-Ser-Tyr-Ser-Nle-Asp-His-D-Phe-Arg-Trp-Lys-Gly-Pro-Val-NH$_2$.

5. A linear alpha-MSH analogue according to claim 2 which is: Ac-Nle-Glu-His-D-Phe-Arg-Trp-Lys-Gly-Pro-Val-NH$_2$.

6. A linear alpha-MSH analogue according to claim 2 which is: Ac-Nle-Asp-His-D-Phe-Arg-Trp-Lys-Gly-Pro-Val-NH$_2$.

7. A linear alpha-MSH analogue according to claim 2 which is: Ac-Nle-Asp-His-D-Phe-Arg-Trp-Gly-NH$_2$.

8. A linear alpha-MSH analogue according to claim 2 which is: Ac-Nle-Glu-His-D-Phe-Arg-Trp-Lys-NH$_2$.

9. A linear alpha-MSH analogue according to claim 2 which is: Ac-Nle-Asp-His-D-Phe-Arg-Trp-Lys-NH$_2$.

10. A linear alpha-MSH analogue according to claim 2 which is: Ac-Nle-Glu-His-D-Phe-Arg-Trp-Orn-NH$_2$.

11. A linear alpha-MSH analogue according to claim 2 which is: Ac-Nle-Asp-His-D-Phe-Arg-Trp-Orn-NH$_2$.

12. A linear alpha-MSH analogue according to claim 2 which is: Ac-Nle-Glu-His-D-Phe-Arg-Trp-Dab-NH$_2$.

13. A linear alpha-MSH analogue according to claim 2 which is: Ac-Nle-Asp-His-D-Phe-Arg-Trp-Dab-NH$_2$.

14. A linear alpha-MSH analogue according to claim 2 which is: Ac-Nle-Asp-His-D-Phe-Arg-Trp-Dpr-NH$_2$.

15. A linear alpha-MSH analogue according to claim 2 which is: Ac-Nle-Glu-His-Phe-Arg-Trp-Lys-NH$_2$.

16. A linear alpha-MSH analogue according to claim 2 which is: Ac-Nle-Asp-His-Phe-Arg-Trp-Lys-NH$_2$.

17. An acetylated linear peptide having the amino acid sequence

AA1 Nle AA2 His AA3 Arg Trp AA4 AA5 wherein AA1 is selected from the group consisting of Ac Ser Tyr Ser, and Ac; Nle is norleucine; AA2 is selected from the group of amino acid residues consisting of Glu and Asp wherein Glu is glutamic acid and Asp is aspartic acid; His is histidine; AA3 is selected from the group of amino acid residues consisting of D-Phe and Phe wherein D-Phe is D-phenylalanine and Phe is phenylalanine; Arg is arginine; Trp is tryptophan; AA4 is selected from the group of amino acid residues consisting of Lys, Gly, Orn, Dab and Dpr wherein Lys is lysine, Gly is glycine, Orn is ornithine, Dab is 2,4 diaminobutyric acid, and Dpr is 2,3 diaminopropionic acid; and AA5 is selected from the group consisting of NH$_2$ and Gly Pro Val NH$_2$ wherein Pro is proline and Val is valine.

18. A linear peptide according to claim 17 which is selected from the group consisting of Ac-Ser Tyr Ser Nle Glu His D-Phe Arg Trp Lys Gly Pro Val-NH$_2$ (SEQ No. 2);

Ac-Ser Tyr Ser Nle Asp His D-Phe Arg Trp Lys Gly Pro Val-NH$_2$ (SEQ No. 3);

Ac-Nle Glu His D-Phe Arg Trp Lys Gly Pro Val-NH$_2$ (SEQ No. 4);

Ac-Nle Asp His D-Phe Arg Trp Lys Gly Pro Val-NH$_2$ (SEQ No. 5);

Ac-Nle Asp His D-Phe Arg Trp Gly-NH$_2$ (SEQ No. 6);

Ac-Nle Glu His D-Phe Arg Trp Lys-NH$_2$ (SEQ No. 7);

Ac-Nle Asp His D-Phe Arg Trp Lys-NH$_2$ (SEQ No. 8);

Ac-Nle Glu His D-Phe Arg Trp Orn-NH$_2$ (SEQ No. 9);

Ac-Nle Asp His D-Phe Arg Trp Orn-NH$_2$ (SEQ No. 10);

Ac-Nle Glu His D-Phe Arg Trp Dab-NH$_2$ (SEQ No. 11);

Ac-Nle Asp His D-Phe Arg Trp Dab-NH$_2$ (SEQ No. 12);

Ac-Nle Asp His D-Phe Arg Trp Dpr-NH$_2$ (SEQ No. 23);

Ac-Nle Glu His Phe Arg Trp Lys-NH$_2$ (SEQ No. 14); and

Ac-Nle Asp His Phe Arg Trp Lys-NH$_2$ (SEQ No. 15).

19. A linear peptide according to claim 18 which is (SEQ No. 2): Ac-Ser Tyr Ser Nle Glu His D-Phe Arg Trp Lys Gly Pro Val-NH$_2$.

20. A linear peptide according to claim 18 which is (SEQ No. 3): Ac-Ser Tyr Ser Nle Asp His D-Phe Arg Trp Lys Gly Pro Val-NH$_2$.

21. A linear peptide according to claim 18 which is (SEQ No. 4): Ac-Nle Glu His D-Phe Arg Trp Lys Gly Pro Val-NH$_2$.

22. A linear peptide according to claim 18 which is (SEQ No. 5): Ac-Nle Asp His D-Phe Arg Trp Lys Gly Pro Val-NH$_2$.

23. A linear peptide according to claim 18 which is (SEQ No. 6): Ac-Nle Asp His D-Phe Arg Trp Gly-NH$_2$.

24. A linear peptide according to claim 18 which is (SEQ No. 7): Ac-Nle Glu His D-Phe Arg Trp Lys-NH$_2$.

25. A linear peptide according to claim 18 which is (SEQ No. 8): Ac-Nle Asp His D-Phe Arg Trp Lys-NH$_2$.

26. A linear peptide according to claim 18 which is (SEQ No. 9): Ac-Nle Glu His D-Phe Arg Trp Orn-NH$_2$.

27. A linear peptide according to claim 18 which is (SEQ No. 10): Ac-Nle Asp His D-Phe Arg Trp Orn-NH$_2$.

28. A linear peptide according to claim 18 which is (SEQ No. 11): Ac-Nle Glu His D-Phe Arg Trp Dab-NH$_2$.

29. A linear peptide according to claim 18 which is (SEQ No. 12): Ac-Nle Asp His D-Phe Arg Trp Dab-NH$_2$.

30. A linear peptide according to claim 18 which is (SEQ No. 13): Ac-Nle Asp His D-Phe Arg Trp Dpr-NH$_2$.

31. A linear peptide according to claim 18 which is (SEQ No. 14): Ac-Nle Glu His Phe Arg Trp Lys-NH$_2$.

32. A linear peptide according to claim 18 which is (SEQ No. 15): Ac-Nle Asp His Phe Arg Trp Lys-NH$_2$.

33. A pharmaceutical preparation for the stimulation of mammalian melanocytes comprising a formulation of at least one compound according to claim 2 or 18 in an amount sufficient to bring about stimulation of melanocytes and in combination with a pharmaceutically acceptable excipient for transdermal administration of said compound.

34. A method for stimulating mammalian integumental melanin synthesis which comprises providing a pharmaceutical composition comprising a formulation comprising of at least one compound according to claim 2 or 18 in an amount sufficient to bring about stimulation of mammalian melanocyte synthesis, in combination with a pharmaceutically acceptable excipient for transdermal administration of said compound.

35. A method according to claim 34 wherein transdermal administration is by oral, nasal or topical means, or by injection of the mammal.

\* \* \* \* \*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ser Tyr Ser Met Glu His Phe Arg Trp Gly Lys Pro Val
1              5                        10

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: position 4 is
        Norleucine; position 7 is D-phenylalaline ( x i ) SEQUENCE DESCRIPTION: SEQ ID NO:2:

```
Ser  Tyr  Ser  Xaa  Glu  His  Xaa  Arg  Trp  Lys  Gly  Pro  Val
1                  5                        10
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 4 is
        Norleucine; position 7 is D-phenylaline ( x i ) SEQUENCE DESCRIPTION: SEQ ID NO:3:

```
Ser  Tyr  Ser  Xaa  Asp  His  Xaa  Arg  Trp  Lys  Gly  Pro  Val
1                  5                        10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline ( x i ) SEQUENCE DESCRIPTION: SEQ ID NO:4:

```
Xaa  Glu  His  Xaa  Arg  Trp  Lys  Gly  Pro  Val
1                  5                        10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline ( x i ) SEQUENCE DESCRIPTION: SEQ ID NO:5:

```
Xaa  Asp  His  Xaa  Arg  Trp  Lys  Gly  Pro  Val
1                  5                        10
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline ( x i ) SEQUENCE DESCRIPTION: SEQ ID NO:6:

Xaa Asp His Xaa Arg Trp Gly
1               5

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline ( x i ) SEQUENCE DESCRIPTION: SEQ ID NO:7:

Xaa Glu His Xaa Arg Trp Lys
1               5

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline ( x i ) SEQUENCE DESCRIPTION: SEQ ID NO:8:

Xaa Asp His Xaa Arg Trp Lys
1               5

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline;
        position 7 is Ornithine ( x i ) SEQUENCE DESCRIPTION: SEQ ID NO:9:

Xaa Glu His Xaa Arg Trp Xaa
1               5

( 2 ) INFORMATION FOR SEQ ID NO:10:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline;
        position 7 is Ornithine ( x i ) SEQUENCE DESCRIPTION: SEQ ID NO:10:

Xaa Asp His Xaa Arg Trp Xaa
1               5

( 2 ) INFORMATION FOR SEQ ID NO:11:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline;
        position 7 is 2,4-diaminobutyric acid ( x i ) SEQUENCE DESCRIPTION: SEQ ID NO:11:

Xaa Glu His Xaa Arg Trp Xaa
1               5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline; position 7
        is 2,4- diaminobutyric acid ( x i ) SEQUENCE DESCRIPTION: SEQ ID NO:12:

Xaa Asp His Xaa Arg Trp Xaa
1               5

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
        Norleucine; position 4 is D-phenylaline;
        position 7 is 2,3-diaminopropionic acid ( x i ) SEQUENCE DESCRIPTION: SEQ ID NO:13:

Xaa Asp His Xaa Arg Trp Xaa
1               5

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

( D ) OTHER INFORMATION: postion 1 is
Norleucine ( x i ) SEQUENCE DESCRIPTION: SEQ ID NO:14:

Xaa Glu His Phe Arg Trp Lys
1                   5

( 2 ) INFORMATION FOR SEQ ID NO:15:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: postion 1 is
Norleucine;

( x i ) SEQUENCE DESCRIPTION: SEQ ID NO:15:

Xaa Asp His Phe Arg Trp Lys
1                   5

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:
        ( D ) OTHER INFORMATION: postion 1 is
Norleucine; position 4 is D-phenylaline ( x i ) SEQUENCE DESCRIPTION: SEQ ID NO:16:

Xaa Glu His Xaa Arg Trp Lys Gly Pro Val
1                   5                   10

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:
        ( D ) OTHER INFORMATION: postion 1 is
Norleucine; position 4 is D-phenylaline ( x i ) SEQUENCE DESCRIPTION: SEQ ID NO:17:

Xaa Glu His Xaa Arg Trp Lys
1                   5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:

( D ) OTHER INFORMATION: postion 1 is
Norleucine; position 4 is D-phenylaline ( x i ) SEQUENCE DESCRIPTION: SEQ ID NO:18:

Xaa Asp His Xaa Arg Trp Lys
1               5

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:
        ( D ) OTHER INFORMATION: postion 1 is
Norleucine; position 4 is D-phenylaline;
position 7 is Ornithine ( x i ) SEQUENCE DESCRIPTION: SEQ ID NO:19:

Xaa Asp His Xaa Arg Trp Xaa
1               5

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:
        ( D ) OTHER INFORMATION: postion 1 is
Norleucine; position 4 is D-phenylaline;
position 7 is 2,4-diaminobutyric acid ( x i ) SEQUENCE DESCRIPTION: SEQ ID NO:20:

Xaa Asp His Xaa Arg Trp Xaa
1               5

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:
        ( D ) OTHER INFORMATION: postion 1 is
Norleucine; position 4 is D-phenylaline;
position 7 is 2,4-diaminopropionic acid ( x i ) SEQUENCE DESCRIPTION: SEQ ID NO:21:

Xaa Asp His Xaa Arg Trp Xaa
1               5

( 2 ) INFORMATION FOR SEQ ID NO:22:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: cyclic ( i i ) MOLECULE TYPE: peptide ( i x ) FEATURE:
                ( D ) OTHER INFORMATION: postion 4 is
                        Norleucine; position 7 is D-phenylaline ( x i ) SEQUENCE DESCRIPTION: SEQ ID NO:22:

Ser  Tyr  Ser  Xaa  Asp  His  Xaa  Arg  Trp  Lys  Gly  Pro  Val
1              5                        10

( 2 ) INFORMATION FOR SEQ ID NO:23:

( i ) SEQUENCE CHARACTERISTICS:
                ( A ) LENGTH: 10 amino acids
                ( B ) TYPE: amino acid
                ( C ) STRANDEDNESS: single
                ( D ) TOPOLOGY: cyclic ( i i ) MOLECULE TYPE: peptide ( i x ) FEATURE:
                ( D ) OTHER INFORMATION: postion 4 is
                        Norleucine; position 7 is D-phenylaline ( x i ) SEQUENCE DESCRIPTION: SEQ ID NO:23:

Ser  Tyr  Ser  Xaa  Asp  His  Xaa  Arg  Trp  Lys
1              5                        10

( 2 ) INFORMATION FOR SEQ ID NO:24:

( i ) SEQUENCE CHARACTERISTICS:
                ( A ) LENGTH: 9 amino acids
                ( B ) TYPE: amino acid
                ( C ) STRANDEDNESS: single
                ( D ) TOPOLOGY: cyclic ( i i ) MOLECULE TYPE: peptide ( i x ) FEATURE:
                ( D ) OTHER INFORMATION: postion 3 is
                        Norleucine; position 6 is D-phenylaline ( x i ) SEQUENCE DESCRIPTION: SEQ ID NO:24:

Tyr  Ser  Xaa  Asp  His  Xaa  Arg  Trp  Lys
1              5

( 2 ) INFORMATION FOR SEQ ID NO:25:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: cyclic ( i i ) MOLECULE TYPE: peptide ( i x ) FEATURE:
                ( D ) OTHER INFORMATION: postion 2 is
                        Norleucine; position 5 is D-phenylaline ( x i ) SEQUENCE DESCRIPTION: SEQ ID NO:25:

Ser  Xaa  Asp  His  Xaa  Arg  Trp  Lys
1              5

( 2 ) INFORMATION FOR SEQ ID NO:26:

( i ) SEQUENCE CHARACTERISTICS:
                ( A ) LENGTH: 7 amino acids
                ( B ) TYPE: amino acid
                ( C ) STRANDEDNESS: single
                ( D ) TOPOLOGY: cyclic ( i i ) MOLECULE TYPE: peptide ( i x ) FEATURE:
( D ) OTHER INFORMATION: postion 1 is
Norleucine; position 4 is D-phenylaline ( x i ) SEQUENCE DESCRIPTION: SEQ ID NO:26:

Xaa Asp His Xaa Arg Trp Lys
1               5

( 2 ) INFORMATION FOR SEQ ID NO:27:

( i ) SEQUENCE CHARACTERISTICS:
( A ) LENGTH: 8 amino acids
( B ) TYPE: amino acid
( C ) STRANDEDNESS: single
( D ) TOPOLOGY: cyclic ( i i ) MOLECULE TYPE: peptide ( i x ) FEATURE:
( D ) OTHER INFORMATION: postion 1 is
Norleucine; position 4 is D-phenylaline ( x i ) SEQUENCE DESCRIPTION: SEQ ID NO:27:

Xaa Asp His Xaa Arg Trp Lys Gly
1               5

( 2 ) INFORMATION FOR SEQ ID NO:28:

( i ) SEQUENCE CHARACTERISTICS:
( A ) LENGTH: 9 amino acids
( B ) TYPE: amino acid
( C ) STRANDEDNESS: single
( D ) TOPOLOGY: cyclic ( i i ) MOLECULE TYPE: peptide ( i x ) FEATURE:
( D ) OTHER INFORMATION: postion 1 is
Norleucine; position 4 is D-phenylaline ( x i ) SEQUENCE DESCRIPTION: SEQ ID NO:28:

Xaa Asp His Xaa Arg Trp Lys Gly Pro
1               5

( 2 ) INFORMATION FOR SEQ ID NO:29:

( i ) SEQUENCE CHARACTERISTICS:
( A ) LENGTH: 10 amino acids
( B ) TYPE: amino acid
( C ) STRANDEDNESS: single
( D ) TOPOLOGY: cyclic ( i i ) MOLECULE TYPE: peptide ( i x ) FEATURE:
( D ) OTHER INFORMATION: postion 1 is
Norleucine; position 4 is D-phenylaline ( x i ) SEQUENCE DESCRIPTION: SEQ ID NO:29:

Xaa Asp His Xaa Arg Trp Lys Gly Pro Val
1               5                   10

( 2 ) INFORMATION FOR SEQ ID NO:30:

( i ) SEQUENCE CHARACTERISTICS:
( A ) LENGTH: 11 amino acids
( B ) TYPE: amino acid
( C ) STRANDEDNESS: single
( D ) TOPOLOGY: cyclic ( i i ) MOLECULE TYPE: peptide ( i x ) FEATURE:
  ( D ) OTHER INFORMATION: position 2 is
    Norleucine; position 5 is D-phenylaline ( x i ) SEQUENCE DESCRIPTION: SEQ ID NO:30:

Ser Xaa Asp His Xaa Arg Trp Lys Gly Pro Val
1               5                       10

( 2 ) INFORMATION FOR SEQ ID NO:31:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: cyclic ( i i ) MOLECULE TYPE: peptide ( x i ) SEQUENCE DESCRIPTION: SEQ ID NO:31:

Ser Tyr Ser Met Glu His Phe Arg Trp Gly Lys Pro Val
1               5                       10

( 2 ) INFORMATION FOR SEQ ID NO:32:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: cyclic ( i i ) MOLECULE TYPE: peptide ( x i ) SEQUENCE DESCRIPTION: SEQ ID NO:32:

Ser Tyr Ser Met Glu His Phe Arg Trp Lys Gly Pro Val
1               5                       10

( 2 ) INFORMATION FOR SEQ ID NO:33:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: cyclic ( i i ) MOLECULE TYPE: peptide ( i x ) FEATURE:
    ( D ) OTHER INFORMATION: position 3 is
      Norleucine; position 6 is D-phenylaline ( x i ) SEQUENCE DESCRIPTION: SEQ ID NO:33:

Thr Ser Xaa Asp His Xaa Arg Trp Lys
1               5

( 2 ) INFORMATION FOR SEQ ID NO:34:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: cyclic ( i i ) MOLECULE TYPE: peptide ( i x ) FEATURE:
    ( D ) OTHER INFORMATION: position 4 is
      Norleucine; position 7 is D-phenylaline ( x i ) SEQUENCE DESCRIPTION: SEQ ID NO:34:

```
Ser  Thr  Ser  Xaa  Asp  His  Xaa  Arg  Trp  Lys
1              5                        10
```